(12) United States Patent
Schendel et al.

(10) Patent No.: US 8,486,694 B2
(45) Date of Patent: Jul. 16, 2013

(54) GENERATION OF ANTIGEN SPECIFIC T CELLS

(75) Inventors: Dolores Schendel, Munich (DE); Susanne Wilde, Munich (DE); Thomas Blankenstein, Berlin (DE)

(73) Assignees: Helmholtz Zentrum Muenchen Deutsches Forschungzentrum fuer Gesundheit und Umwelt GmbH, Neuherberg (DE); Max-Delbrueck-Centrum fuer Molekulare Medizin, Berlin (DE)

( * ) Notice: Subject to any disclaimer, the term of this patent is extended or adjusted under 35 U.S.C. 154(b) by 798 days.

(21) Appl. No.: 11/990,054

(22) PCT Filed: Aug. 4, 2006

(86) PCT No.: PCT/EP2006/007752
§ 371 (c)(1),
(2), (4) Date: Mar. 22, 2010

(87) PCT Pub. No.: WO2007/017201
PCT Pub. Date: Feb. 15, 2007

(65) Prior Publication Data
US 2010/0189728 A1 Jul. 29, 2010

(30) Foreign Application Priority Data

Aug. 5, 2005 (EP) .................................. 05017128
Apr. 10, 2006 (EP) .................................. 06007539

(51) Int. Cl.
*C12N 5/10* (2006.01)

(52) U.S. Cl.
USPC ......................... 435/347; 435/7.24; 435/455

(58) Field of Classification Search
None
See application file for complete search history.

(56) References Cited

U.S. PATENT DOCUMENTS

| 6,805,861 | B2 | 10/2004 | Stauss | |
| 7,659,084 | B2 * | 2/2010 | Frentsch et al. | 435/7.24 |
| 2002/0090362 | A1 | 7/2002 | Stauss | |

FOREIGN PATENT DOCUMENTS

| WO | WO 97/26328 | 7/1997 |
| WO | WO 2004027428 A1 * | 4/2004 |

OTHER PUBLICATIONS

Drexler et al., Cancer Res 1999;59:4955-4963.*
Voss et al., Bone Marrow Transplantation (2000) 25, Suppl. 2, S43-S45.*
Rosenberg et al., Nature Medicine vol. 10, No. 9, Sep. 2004, pp. 909-915.*
Janeway et al., Immunobiology, 5th ed., 2001, Garland Publishing, pp. 116-117 and 174-176.*
Gelder et al., International Immunology, vol. 10, No. 2, pp. 211-222 (1998).*
Belmares et al., The Journal of Immunology, 2002, 169: 5109-5117.*
Nuckel et al., Blood. 2005;105:1694-1698 prepublished online Oct. 5, 2004.*
Goldsby et al., Immunology, 5th ed., 2002, W.H. Freeman and Co., pp. 172-177.*
Dawicki et al. (Eur J Immunol. Mar. 2004;34(3):743-51).*
Marzio et al. (Immunopharmacol Immunotoxicol. Aug. 1999;21(3):565-82).*
Mutis et al., Blood, Jul. 15, 2002_vol. 100, No. 2, pp. 547-552.*
Becker et al., "Adoptive tumor therapy with T lymphocytes enriched through an IFN-γ capture assay," Nature Med., vol. 7, No. 10, pp. 1159-1162 (2001).
Britten et al., "Identification of T cell epitopes by the use of rapidly generated mRNA fragments," Journal of Immunological Methods, vol. 299, No. 1-2, pp. 165-175 (Apr. 2005).
Britten et al., "The use of clonal mRNA as an antigenic format for the detection of antigen-specific T lymphocytes in IFN-γ ELISPOT assays," Journal of Immunological Methods, vol. 2871 No. 1-2, pp. 125-136 (Apr. 2004).
Britten et al., "The use of HLA-A 0201-transfected K562 as standard antigen-presenting cells for CD8+ T lymphocytes in IFN-γ ELISPOT assays," Journal of Immunological Methods, vol. 259, No. 1-2, pp. 95-110 (Jan. 2002).
Clay et al., "Efficient transfer of a tumor antigen-reactive TCR to human peripheral blood lymphocytes confers anti-tumor reactivity," Journal of Immunology, vol. 163, No. 1, pp. 507-513 (Jul. 1999).
Ding et al., "Combined transfection with EBV-specific epitopes and HLA-A2 genes is more effective than separate transfection in promoting CTL lysis against nasopharyngeal carcinoma," Cellular & Molecular Immunology, vol. 1, No. 3, pp. 229-234 (Jun. 2004).
Dudley et al., "Adoptive-cell-transfer therapy for the treatment of patients with cancer," Nature Reviews Cancer, vol. 3, No. 9, pp. 666-675 (Sep. 2003).
Dudley et al., "Cancer regression and autoimmunity in patients after clonal repopulation with antitumor lymphocytes," Science, vol. 298, pp. 850-854 (2002).
Dupont et al., "Artificial antigen-presenting cells transduced with telomerase efficiently expand epitope-specific, human leukocyte antigen-restricted cytotoxic T cells," Cancer Research, vol. 65, No. 12, pp. 5417-5427 (Jun. 2005).
Engels et al., "Redirecting Human T Lymphocytes Toward Renal Cell Carcinoma Specificity by Retroviral Transfer of T Cell Receptor Genes," Human Gene Ther., vol. 16, No. 7, pp. 799-810 (2005).
Gao et al., "Allo-major histocompatibility complex-restricted cytotoxic T lymphocytes engraft in bone marrow transplant recipients without causing graft-versus-host disease," Blood, vol. 94, No. 9, pp. 2999-3006 (Nov. 1999).

(Continued)

*Primary Examiner* — Zachary Skelding
(74) *Attorney, Agent, or Firm* — Jenkins, Wilson, Taylor & Hunt, P.A.

(57) ABSTRACT

The present invention is directed to a method of generating antigen specific T cells. Furthermore, the invention is directed to antigen specific T cells, isolated transgenic TCR's, pharmaceutical compositions containing same and their use in adoptive cell therapy. This invention in particular pertains to the use of cells co-expressing allogeneic MHC molecules and antigens to induce peptide-specific T cells from non-selected allogeneic T cell repertoires.

17 Claims, 15 Drawing Sheets

OTHER PUBLICATIONS

Gao et al., "Selective elimination of leukemic CD34+ progenitor cells by cytotoxic T lymphocytes specific for WT1," Blood, vol. 95, pp. 2198-2203 (2000).

Geiger et al., "A generic RNA-pulsed dendritic cell vaccine strategy for renal cell carcinoma," J. Translational Medicine, vol. 3, No. 29, pp. 1-15 (in press) (2005).

Gilboa and Viewig, "Cancer immunotherapy with mRNA-transfected dendritic cells," Immunol. Rev., vol. 199, pp. 251-263 (2004).

Greten et al., "Peptide-beta2-microglobulin-MHC fusion molecules bind antigen-specific T cells and can be used for multivalent MHC-Ig complexes," Journal of Immunological Methods, Elsevier, Amsterdam, NL, vol. 271, No. 1-2, pp. 125-135 (Dec. 2002).

Javorovic et al., "RNA transfer by electroporation into mature dendritic cells leading to reactivation of effector-memory cytotoxic T lymphocytes: a quantitative analysis," Molecular Therapy: The Journal of the American Society of Gene Therapy, vol. 12, No. 4, pp. 734-743 (May 2005).

Kolb et al., "Graft-versus-leukemia effect of donor lymphocyte transfusions in marrow grafted patients," Blood, vol. 86, p. 2041 (1995).

Kolb et al., "Graft-versus-leukemia reactions in allogeneic chimeras," Blood, vol. 103, pp. 767-776 (2004).

Latouche et al., "Induction of human cytotoxic T lymphocytes by artificial antigen-presenting cells," Nature Biotechnology, vol. 18, No. 4, pp. 405-409 (Apr. 2000).

Levings et al., "Phenotypic and functional differences between human CD4+CD25+ and type I regulatory T cells," Curr. Top. Microbial. Immunol., vol. 293, pp. 303-326 (2005).

Liao et al., "Transfection of RNA encoding tumor antigens following maturation of dendritic cells leads to prolonged presentation of antigen and the generation of high-affinity tumor-reactive cytotoxic T lymphocytes," Mol. Ther., vol. 9, pp. 757-764 (2004).

Morgan et al., "High efficiency TCR gene transfer into primary human lymphocytes affords avid recognition of melanoma tumor antigen glycoprotein 100 and does not alter the recognition of autologous melanoma antigens," Journal of Immunology, vol. 171, No. 6, pp. 3287-3295 (Sep. 2003), Nair et al., "Induction of primary carcinoembryonic antigen (CEA)-specific cytotoxic T lymphocytes in vitro using human dendritic cells transfected with RNA," Nat. Biotechnol., vol. 16, No. 4, pp. 364-369 (1998).

Napolitani et al., "Selected Toll-like receptor agonist combinations synergistically trigger a T helper type-I polarizing programme in dendritic cells," Nat. Immunol., vol. 6, No. 8, pp. 769-76 (2005).

Notification of Transmittal of International Preliminary Report on Patentability corresponding to International Application No. PCT/EP2006/007752 dated Sep. 27, 2007.

Notification of Transmittal of International Search Report and the Written Opinion of the International Searching Authority, or the Declaration corresponding to International Application No. PCT/EP2006/007752 dated Jan. 23, 2007.

Oelke et al., "Technological advances in adoptive immunotherapy," Drugs of Today, vol. 41, No. 1, pp. 13-21 (Jan. 2005).

Palermo et al., "Qualitative difference between the cytotoxic T lymphocyte responses to melanocyte antigens in melanoma and vitiligo," Eur. J. Immunol., vol. 35, pp. 3153-3162 (2005).

Papanicolaou et al., "Rapid expansion of cytomegalovirus—specific cytotoxic T lymphocytes by artificial antigen-presenting cells expressing a single HLA allele," Blood, vol. 102, No. 7, pp. 2498-2505 (Oct. 2003).

Regn et al., "Ex vivo generation of cytotoxic T lymphocytes specific for one or two distinct viruses for the prophylaxis of patients receiving an allogeneic bone marrow transplant," Bone Marrow Transplant, vol. 27, pp. 53-64 (2001).

Schaft et al., "Generation of an optimized polyvalent monocyte-derived cell vaccine by transfecting defined RNA after rather than before maturation," J. Immunol., vol. 174, No. 5, pp. 3087-3097 (2005).

Schendel et al., "Human CD8+ T lymphocytes. 1997," In: *The Immunology Methods Manual*, I. Letkovits, Ed., pp. 670-690, Academic Press Ltd., London.

Schendel et al., "Standardization of the human in vitro cell-mediated lympholysis technique," Tissue Antigens, 13, pp. 112-120 (1979).

Su et al., "Antigen presenting cells transfected with LMP2a RNA induce CD4+ LMP2a-specific cytotoxic T lymphocytes which kill via a Fas-independent mechanism," Leuk. Lymphoma, vol. 43, No. 9, pp. 1651-1662 (2002).

Su et al., "The generation of LMP2a-specific cytotoxic T lymphocytes for the treatment of patients with Epstein-Barr virus-positive Hodgkin disease," Eur. J. Immunol., vol. 31, pp. 947-958 (2001).

Toes et al., "CD4-CD40Ligand interactions and their role in cytotoxic T lymphocyte priming and anti-tumor immunity," Semin. Immunol., vol. 10, No. 6, pp. 443-448 (1998).

Wolfl et al., "Quntitation of MHC Tetramer-Positive Cells From Whole Blood: Evaluation of a Single-Platform, Six-Parameter Flow Cytometric Method," Wiley-Liss, Inc., Cytometry, Part A, vol. 57A, pp. 120-130 (2004).

Yee et al., "Isolation of High Avidity Melanoma-Reactive CTL from Heterogeneous Populations Using Peptide-MHC Tetramers," The Journal of Immunology, vol. 162, No. 4, pp. 2227-2234 (1999).

Zhao Yangbing et al., "Primary human lymphocytes transduced with NY-E50-1 antigen-specific TCR genes recognize and kill diverse human tunior cell lines," Journal of Immunology, vol. 174, No. 7, pp. 4415-4423 (Apr. 2005).

European Search Report corresponding to European Patent Application No. 10179257.0-1222 dated Oct. 26, 2010.

Falk et al., "Allogeneic MHC class I ligands and their role in positive and negative regulation of human cytotoxic effector cells," Human Immunol., vol. 63, pp. 8-19 (2002).

\* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Artifically synthesized YMD tyrosinase peptide

<400> SEQUENCE: 1

Tyr Met Asp Gly Thr Met Ser Gln Val
1               5
```

GENERATION OF ANTIGEN SPECIFIC T CELLS

The present invention is directed to a method of generating antigen specific T cells. Furthermore, the invention is directed to antigen specific T cells, isolated transgenic T cell receptors (TCRs), pharmaceutical compositions containing same and their use in adoptive cell therapy. This invention in particular pertains to the use of cells co-expressing allogeneic MHC molecules and antigens to induce peptide-specific T cells from non-selected allogeneic T cell repertoires.

The adoptive transfer of lymphocytes in the setting of allogeneic stem cell transplantation (SCT) has demonstrated the power of the immune system for eradicating hematological malignancies (Kolb et al. 1995). It appears that SCT can also function to eliminate solid tumors, such as renal cell carcinomas (RCC) in some cases (reviewed in Kolb et al. 2004 and Dudley and Rosenberg, 2003). In SCT recipients, the elimination of malignant cells may only occur after several months up to a year, due to the fact that specific T cells must be activated in vivo and must then expand to adequate numbers following the development of the new hematopoietic system in the transplant recipient. Alternatively, after a period of time (approximately 60 days) during which tolerance is established in the SCT recipient, a transfer of unprimed, unseparated lymphocytes can be made to speed up the generation of immune responses directed against tumor cells. Here again, the specific lymphocytes capable of attacking tumor cells must be activated and expanded from the low frequency precursor lymphocytes that are present among the unselected population of lymphocytes that are transferred. Donor lymphocyte infusions (DLI) of unselected lymphocyte populations after SCT work well for the elimination of chronic myelogenous leukemia (CML), which grows slowly, but are less effective in the eradication of acute leukemia, partly due to the fact that the growth of the malignant cells outpaces the expansion capacity of the immune cells. This same expansion differential also impacts on the poor immune elimination of rapidly progressing solid tumors. A second handicap in the use of unselected lymphocyte populations in DLI is that T cells may also be transferred that have the capacity to attack normal cells and tissues of the recipient, leading to graft-versus-host-disease (GVHD), a disease with high morbidity and mortality.

Recent studies have demonstrated that the adoptive transfer of selected T cells with defined peptide specificities can lead to major reductions in tumor burden in an autologous setting, particularly if patients have been pretreated with non-myeloablative regimens (Dudley et al. 2002, 2003). This eliminates the need to perform SCT in the tumor patient, and thereby also bypasses the problem of GVHD. Effective immune responses were seen in pretreated melanoma patients who received autologous mixtures of tumor-infiltrating lymphocytes (TIL). These mixtures of cells, containing both CD4 and CD8 positive T cells, appear to be clinically more efficacious than the adoptive transfer of large numbers of a single CD8 T cell clone specific for a particular MHC-tumor-associated antigen (TAA) ligand. One factor contributing to this difference is the requirement to have CD4 T cells to maintain long-lived CD8 T cells. Furthermore, immune responses directed against single ligands can lead to the selection of tumor cell variants that have lost expression of the corresponding ligand and thereby can escape immune detection. On the one hand, transfer of complex mixtures of T cells, as they are present among tumor infiltrating lymphocytes, can overcome these problems by providing CD4 and CD8 cells with multiple specificities but they can also lead to autoimmunity if the mixtures of TIL contain T cells that recognize ligands expressed by normal tissues. This is demonstrated for example by the attack of normal melanocytes leading to vitiligo in melanoma patients following adoptive cell therapy (ACT) using cells that recognize melanoma differentiation antigens that are also expressed in melanocytes (Dudley et al. 2002).

In order to extend the capacity to use ACT to treat patients with more rapidly growing tumors, it is a goal to transfer enriched, peptide-specific effector T cells (both CD4 T helper cells and cytotoxic T lymphocytes) that have been selected for their ligand specificities to effectively attack tumor cells while avoiding serious attack of normal tissues. These cells are to be rapidly expanded to large numbers ex vivo and then used for ACT. Alternatively, the T cell receptors (TCR) of such ligand-specific T cells can be cloned and expressed as TCR-transgenes in activated lymphocytes, using either recipient peripheral blood lymphocytes or activated T cell clones with defined specificities that grow well and do not have the capacity to attack normal host tissues.

As examples, an expanded allospecific T cell clone that is specific for an MHC molecule not expressed by the recipient or an expanded T cell clone specific for a virus, such as cytomegalovirus or Epstein-Barr virus, could be used as recipient cells for the transgenic TCR. The availability of a panel of transgenic TCR vectors, recognizing different MHC-peptide ligands could be used to develop large numbers of pre-activated T cells of both the CD4 and CD8 subtypes, thereby allowing large numbers of effector lymphocytes to be rapidly prepared and transferred to patients whose tumors express the corresponding TCR ligands. This would save time in achieving the numbers of specific T cells required to control tumor growth, possibly leading to more effective tumor eradication of rapidly progressing tumors.

Because the determinants that specific T cells recognize on leukemia and lymphomas, as well as solid tumor cells, often represent self-peptides derived from over-expressed proteins that are presented by self-MHC molecules, the affinity of their T cell receptors (TCR) is low, since T cells bearing high affinity receptors have been eliminated through the process of negative selection which is applied to lymphocytes during their development in the thymus. More effective tumor cell recognition occurs if the T cells are generated from lymphocyte populations that have not been negatively selected against self-MHC-molecules during their development in the thymus.

Therefore, there is an important need to find means to rapidly generate T cells that bear TCR with high functional avidity that have the capacity to recognize their ligands on tumor cells. Such T cells are present in the repertoire of an allogeneic individual who has MHC-mismatches to the potential ACT recipient.

The work of Stauss and coworkers (Gao et al., 1999, 2000) has shown that cytotoxic effector cells that are selected to recognize peptides derived from the transcription factor, WT-1, and presented by allogeneic MHC class I molecules have high affinity TCR and can effectively eliminate WT-1 positive leukemia without damaging normal stem cells. In the setting of a partial-mismatched SCT, tolerance for such T cells can be established, allowing their specific adoptive transfer. Stauss solved the problem of obtaining such allo-restricted CD8 T cells by using the T2 cell line, pulsed with WT-1 peptides, as a source of stimulating cells. T2 cells have gene deletions that impair their ability to load endogenous peptides into their MHC class I molecules and due to deletions in chromosome 6, these cells have the limited capacity to express HLA-A2 molecules. When peptides are provided exogenously to T2 cells they can bind to the empty HLA-A2 molecules and form stable complexes at the cell surface. These peptide-pulsed cells can then be used to stimulate peripheral blood lymphocytes from an HLA-A2-negative individual. Under such priming conditions a number of different activated lymphocyte populations emerge in vitro. T cells recognizing HLA-A2 molecules are activated, a fraction of which are specific for the WT-1/HLA-A2 ligand. These sought-after T cells must be separated from T cells that recognize HLA-A2 molecules irrespective of peptide. Unfortunately, the failure of T2 cells to express a normal complement of MHC class I molecules, as well as its inherent capacity to activate non-MHC-restricted cells, leads to a parallel activation of NK and NK-like T cells (Falk et al 2002). These populations often dominant the cultures and it requires tedious work to eliminate these cells and to enrich the T cell populations for the desired alloreactive cells. This slows the process of generation of specific T cells and therefore causes significant clinical restrictions. Furthermore, the peptides from the antigens must be known in advance since they must be pulsed onto T2 cells from the outside since T2 cells lack the transporter-associated with antigen processing (TAP) genes which allow antigen presenting cells to generate peptides from proteins expressed within the cell and present them on their surface in MHC class I and class II molecules. Furthermore, T2 only express endogenous HLA-A2 class I molecules.

US Patent Application 20020090362 discloses a method of treating a patient, the method comprising administering to the patient a therapeutically effective amount of cytotoxic T lymphocytes (CTL) which recognise at least part of an antigenic molecule when presented by an HLA class I (or equivalent) molecule on the surface of a cell wherein the cytotoxic T lymphocytes are not derived from the patient. This application describes the use of stimulating cells which are allogenic or even xenogenic in view of the donor of the CTL. US Patent Application 20020090362 further discloses stimulating cells which are preferably incapable of loading a selected molecule (peptide) and in particular the use of TAP deficient stimulating cells.

U.S. Pat. No. 6,805,861 describes a method of making a clonal population of cytotoxic T lymphocytes (CTL) reactive against a selected molecule the method comprising the step of (a) co-culturing a sample containing CTL derived from a healthy individual (i.e. which are not derived from the patient) with a stimulator cell which expresses HLA class I (or equivalent) molecules on its surface and that presents at least a part of a selected (antigenic) molecule on the surface of said stimulator cell and (b) selecting a CTL clone reactive against said selected molecule when at least a part of said molecule is presented by an HLA class I (or equivalent) molecule on the surface of a cell. The considerations mentioned for US Patent Application 20020090362 also apply here.

Therefore, it is a problem underlying the present invention to generate T cells that bear TCR with high functional avidity that have the capacity to recognize their MHC-peptide ligands on pathogenic agents, as for example tumor cells. It is a further problem underlying the present invention to provide a method for the rapid and effective generation of antigen specific T cells which can be used in adoptive cell transfer. Furthermore, it is a problem underlying the invention to provide a T cell based pharmaceutical composition that can be used for treating a patient suffering from a disease without a risk of graft-versus-host-disease (GVHD).

The inventors have developed an alternative strategy to obtain allorestricted, peptide-specific T cells. Well known technologies to express proteins in dendritic cells (DCs), or other cells that can function as antigen-presenting cells (APCs), through the transfer of in vitro transcribed RNA (Nair et al. 1998) were used. However, instead of expressing only RNA encoding sources of antigens, as is common in the prior art, the inventors co-transfected RNA encoding a specific target molecule, such as tyrosinase as a model TAA, and an RNA encoding an allogeneic MHC molecule, for example HLA-A2, into DCs, or other cells, derived from an HLA-A2 negative donor.

These transfected DC can then be used to prime PBL, for example autologous PBL. The HLA-A2-antigen ligands represent allo-determinants for the PBL of the HLA-A2 negative DC donor and therefore T cells bearing high affinity TCR can be obtained. Because the DCs express a full complement of self-MHC molecules, the emergence of non-MHC-restricted populations of lymphocytes is suppressed through negative MHC regulation. A number of different strategies can be used to enrich the peptide-specific/HLA-A2 allorestricted T cells from T cells that recognize HLA-A2 independently of the specific peptide derived from the antigen, including cytokine capture, tetramer selection or by cloning of individual T cells that are subsequently expanded.

The present approach offers a number of advantages over the T2 system or *Drosophila* cells for obtaining allorestricted peptide-specific T cells (as described by Stauss and coworkers).

Firstly, T cells with allorestriction for a variety of MHC molecules can be developed since in vitro transcribed RNA for any cloned MHC class I or class II allele can be utilized. Thus, such APC can be used to generate both allorestricted peptide-specific CD4 and CD8 T cells via presentation of desired antigens through transferred allogeneic MHC class II or allogeneic MHC class I alleles, respectively. It is noted that the approach described in US Patent Application 20020090362 is only suitable for generating CD8 T cells.

Second, one is not restricted to priming against only known peptides of selected TAA since the whole antigen is available for processing and presentation within the DC. The antigen can be provided either in the form of protein or in the form of nucleic acid which will be subsequently used as the template to express the corresponding protein in the APC. Also here, the differences to the prior art approaches are striking: in US Patent Application 20020090362, the peptides are loaded onto stimulating cells (which are not professional APC's), since the stimulating cells are unable to process and present antigens. Thus, only known peptides can be used in this approach and not antigens of unknown structure as it is the case in the present invention.

Third, the TCR sequences of these selected T cells with high functional avidity can be used for expression in autologous PBMC to generate TCR transgenic T cells with high functional avidity for tumors that bear the respective TCR ligands. ACT can be performed using such TCR-transgenic T cells as an alternative to the adoptive transfer of specific lymphocytes that must be isolated and expanded over considerable periods of time in vitro. This would allow treatment of patients not undergoing SCT as well as application in patients with other non-hematological malignancies expressing the corresponding MHC-peptide ligands seen by the transgenic TCRs.

In particular, the present invention provides a method for the generation of antigen specific T cells wherein APC's are used which are derived from a healthy donor and which are autologous to PBL which are also derived from the same healthy donor. The MHC molecule transfected into said APC's however is patient derived. Patient derived in this context means that the sequences encoding same are directly obtained from the patient or alternatively are derived from another source, for example cDNA or genomic clones, which are identical to the MHC alleles of the patient to be treated. Furthermore, for the first time, the present invention uses the approach to co-transfect MHC molecule and antigen into those APC's in general in order to achieve the desired antigen specific T cells.

The transfected APC's of the invention can be used to prime PBL which are autologous in view of the APC's. The transferred MHC-antigen ligands represent allo-determinants for the PBL of the APC donor who does not carry the MHC gene corresponding to said MHC molecule that is transferred into the APC. Therefore T cells bearing high affinity TCR can be obtained. Because the APCs express a full complement of self-MHC molecules, the emergence of non-MHC-restricted populations of lymphocytes is suppressed through negative MHC regulation. The use of APCs, and the use of DCs in particular, in this invention is of particular importance because these cells can efficiently process and present peptides in their MHC class I and class II molecules. In addition, APCs are characterized by the expression of additional costimulatory molecules that allow them to signal additional receptors on T lymphocytes that lead to optimal activation, expansion and survival of T cells. Furthermore, APCs and DCs in particular have the capacity to secrete a variety of cytokines and chemokines that impinge on the function of the primed lymphocytes. Dependent upon the factors made by the APCs the responding lymphocytes can be modified with respect to their subtype, homing capacity and functional capacities. As examples, mature DCs can be used to activate T cells that have the desired antigen-specificity due to the interactions of their TCR with the MHC-peptide ligands displayed by the DC but also have desired functions based on the cytokines/chemokines secreted by the particular DCs used as APCs. DCs secreting different types of cytokines/chemokines can be generated in vitro and used to stimulate desired types of T cells. Thus, mature DCs that are generated in culture with maturation cocktails that lead them to secrete high amounts of the cytokine IL-12 have a good capacity to activate CD4 T cells of the T helper type 1 which are particularly important in anti-tumor immunity (Napolitani et al. 2005). In contrast, immature DCs, that secrete IL-10, seem to be particularly potent in activating regulatory T cells that can suppress the activities of other lymphocytes (Levings and Roncarola, 2005). Such regulatory T cells may thereby be of clinical benefit in controlling autoagressive T cells in patients suffering from autoimmune diseases such as type 1 diabetes mellitus or in controlling immune responses to pathogens that become too overriding and cause immune pathology, as for example in some forms of leprosy.

Because DCs have the capacity to process and present antigens that are expressed in various compartments within the cell it is not necessary to know the exact antigen peptides in order to generate T cells with the desired antigen specificity. For example, when DCs are provided with full protein antigens, or RNA encoding such proteins, they can process several different peptides from one and the same protein and present them in their MHC class I and II molecules; these various MHC-peptide ligand can in turn prime different populations of CD4 and CD8 T cells. There is no reason why DCs can not be modified to express an allogeneic MHC class I and an allogeneic MHC class II molecule at the same time as they are modified to express antigen, thereby allowing priming of both CD4 and CD8 allorestricted T cells in the same cultures. Interactions of the activated CD4 T cells with the DCs can in turn provide them with signals that allow them to optimally activate CD8 T cells (Toes et al. 1998). DCs further can be modified to express several different antigens simultaneously; in fact DCs can be transfected to express the entire RNA contents of a tumor cell, encompassing many hundreds of RNA species. The DCs are capable of processing and presenting multiple MHC class I and class II ligands simultaneously on their surface, leading to activation of many different T cell types (Gilboa and Viewig, 2004; Geiger et al. 2005; Schaft et al. 2005). There is no reason why this same property can not be captured to create allorestricted MHC-peptide ligands by co-expressing allogeneic MHC class I and/or class II molecules simultaneously with the mixtures of RNA or proteins for antigens.

The present invention is supported by the following experimental results:

1) First, the inventors showed that when RNA encoding an allogeneic MHC molecule, such as HLA-A2, is transferred into cells of an HLA-A2-negative donor, it can be demonstrated that HLA-A2 molecules are expressed at the cell surface, as detected using flow cytometry following staining with HLA-A2-specific monoclonal antibodies. Furthermore, these cells can activate an HLA-A2 allospecific T cell clone (JB4 cells) to secrete cytokine (IFN-gamma), demonstrating their functional capacity. Transfer and expression can be achieved in DCs as well as in other cells, such as K562 cells.

2) Likewise, when RNA encoding a tumor-associated antigen (TAA) such as tyrosinase as an example of a TAA for melanoma is transferred, one can detect protein expression inside the cells, since this is a non-membrane protein. This protein expression can be demonstrated using flow cytometry and intracellular staining using tyrosinase-specific antibodies and secondary fluorescent-labeled antibodies for detection. Transfer and expression can be achieved in DCs and in other cells such as K562.

3) When one transfers both species of RNA (HLA-A2 plus tyrosinase) into the same cells, then one can detect simultaneous expression of both types of protein in the recipient cells. This can be achieved in DCs and other cells like K562.

4) The APCs co-expressing an MHC molecule, such as HLA-A2, and a TAA, such as tyrosinase, generate MHC-peptide complexes and display them on their surface in a manner with which they can interact with T cells bearing TCR for the corresponding ligand. This is demonstrated by the fact that such co-expressing APC can activate a T cell clone with the specificity as measured by cytokine release. This was demonstrated using either DCs or other cells such as K562 as APC for an HLA-A2-tyrosinase-peptide specific CD8 T cell clone (Tyr-F8 cells).

In particular, the present invention is directed to the following aspects and embodiments:

According to a first aspect, the present invention provides a method of generating antigen specific T cells comprising the steps of a) providing a nucleic acid encoding a patient-derived MHC molecule and an antigen or a nucleic acid encoding said antigen;

b) co-transfecting or introducing both compounds as defined in a) in antigen presenting cells (APC's) derived from a healthy donor, preferably from dendritic cells;

c) priming peripheral blood lymphocytes (PBL's) derived from the healthy donor with said APC's;

d) selecting those T cells which are specific for the MHC antigen ligand.

The APC's are preferably selected from dendritic cells, activated B cells, monocytes, macrophages, activated T cells, hematological malignancies with antigen presenting capacities and/or EBV-transformed lymphoblastoid cell lines.

Dendritic cells (DC) are in particular preferred. Mature dendritic cells (DCs) express both MHC class I and class II molecules at high levels, along with a wide variety of costimulatory molecules, which provide them with the full capacity to prime naïve T cells that have not encountered antigen previously. They also have all the necessary genes/proteins that allow them to process and present antigens form intracellular proteins in their MHC class I and class II molecules. Thus, they are optimal antigen presenting cells (APCs) to use as stimulating cells for induction of both CD4 and CD8 T cells responses. Expression of RNA encoding a TAA in autologous DCs allowed tumor antigen specific T cells with high affinity to be primed in vitro using peripheral blood lymphocytes of the same healthy donor (Liao et al. 2004). Because DCs express a normal complement of self-encoded MHC class I molecules they can negatively regulate the activity of NK and NK-like T cells, in contrast to T2 cells or cells of other species, such as *Drosophila* cells.

According to an embodiment, the MHC molecule and the antigen are used as a mixture of antigen and nucleic acid encoding the MHC molecule. As an alternative, the nucleic acid encoding an allogeneic MHC molecule and the antigen are provided as bicistronic RNA.

The antigens against which specific T cells should be generated are preferably selected from pathogenic agents derived from viruses, bacteria, protozoa, and parasites as well as tumor cells or tumor cell associated antigens, autoantigens or functional parts thereof.

The viruses are preferably selected from the group consisting of influenza viruses, measles and respiratory syncytial viruses, dengue viruses, human immunodeficiency viruses, human hepatitis viruses, herpes viruses, or papilloma viruses. The protozoa may be *Plasmodium falciparum*, the bacteria tuberculosis-causing Mycobacteria.

The tumor associated antigen is preferably selected from hematological malignancies or solid tumors, more preferably colon carcinoma, breast carcinoma, prostate carcinoma, renal cell carcinoma (RCC), lung carcinoma, sarcomas or melanoma cells.

The selection step d) is preferably performed by means of measuring the cytokine release of the T cells or other measures of T cell activation. For example, the activated T cells can be cloned as individual cells and following expansion, the T cell clones can be analyzed for their MHC-peptide specificity and those with the desired specificity can be selected for further use (Schendel et al. 1979, 1997). Alternatively, soluble MHC-peptide ligands in various forms, such as tetramers, can be marked with a fluorescent label and incubated with the activated T cells. Those T cells bearing TCR that interact with the tetramers can then be detected by flow cytometry and sorted on the basis of their fluorescence (Yee et al. 1999). Furthermore, T cells can be stimulated for short periods of time with tumor cells to which they should react and their interferon gamma secretion detected by capture reagents, for example as published (Becker et al. 2001).

According to a preferred embodiment, the method of the invention further comprises the step of expanding the T cells selected in d) ex vivo. This can be done by co-culturing the selected T cells with APC generated in the same manner as used for their initial priming, adding new APC to the T cell cultures every 7-10 days and providing the cells with fresh culture medium on a regular basis that contains supplementary cytokines, dependent upon the type of T cell that one is expanding, this can include IL-2, IL-4, IL-7 and/or IL-15 among others, as described in (Schendel et al., 1997; Regn et al. 2001; Su et al. 2001, 2002).

Further, the method of the invention further comprises the step of cloning the T cell receptor (TCR) of the isolated T cells and/or expressing the TCR transgenes in PBMC. This can be done according to established methods such as those described in Engels et al., 2005.

It is one major advantage of the present approach that it is not restricted to a specific MHC class. Thus, the MHC molecule may be selected from MHC class I, preferably HLA-A, HLA-B, HLA-C or HLA-E, or MHC class II, preferably HLA-DP, HLA-DQ, HLA-DR as long as they correspond to the MHC type of the patient.

According to a second aspect, the present invention provides an antigen specific T cell, which is obtainable by the method as defined above.

Said T cell preferably is a T cell with effector cell characteristics, more preferably a cytokine producing T cell, a cytotoxic T cell or regulatory T cell, preferably CD4+ or CD8+ T cells.

In a third aspect, the invention is directed to a nucleic acid coding for a transgenic TCR, which is obtainable by the method as explained above.

An additional aspect is directed to a vector, which comprises the nucleic acid coding for a transgenic TCR. This vector is preferably an expression vector which contains a nucleic acid according to the invention and one or more regulatory nucleic acid sequences. Preferably, this vector is a plasmid or a retroviral vector.

The invention further comprises a PBMC, which has been transformed with the vector as defined above.

In a further aspect, the present invention provides a pharmaceutical composition, which comprises the T cells or PBMCs as explained above and a pharmaceutically acceptable carrier.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition can contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection or a vaccine.

According to a further aspect, the present invention is directed to the use of the antigen specific T cells or PBMCs as explained above for the manufacture of a medicament for adoptive cell therapy and in particular for treating hematological malignancies or solid tumors and acute or chronic infections (see also above).

The present invention is illustrated by examples and figures in the following.

The figures are showing the following:

EXAMPLES

Description of Experiments and Figures

Figure 1:
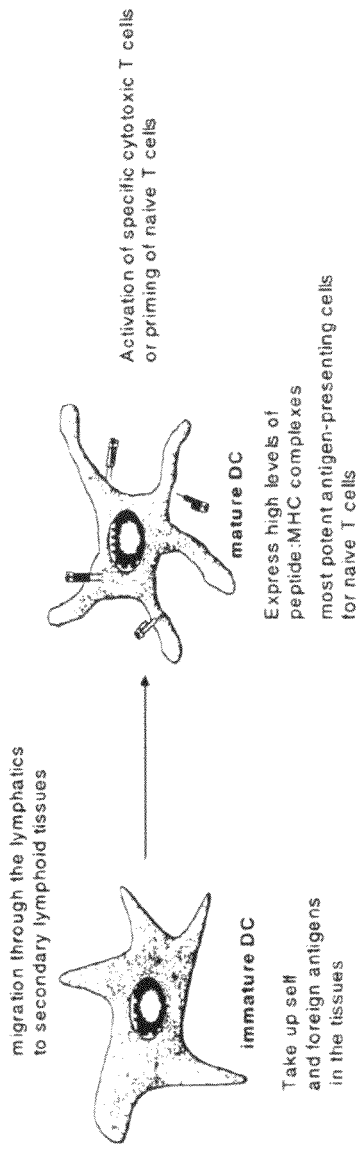
FIG. 1 is showing the maturation of dendritic cells and activation of specific cytotoxic T cells in the conventional immune response against malignant cells.

FIG. 1. Immature and Mature Stages of Dendritic Cells

Dendritic cells (DCs) are considered to be the most "professional" of antigen-presenting cells (APC) because of their capacity to activate T cells that have never encountered antigen (naïve T cells). This is dependent upon several factors that have already been discovered for DCs and may also be dependent upon characteristics that are still to be identified. There are various forms of DCs and their unique characteristics are continually in the process of investigation. The type of DC that is used most commonly for clinical studies is a myeloid DC that can be differentiated from CD14-positive blood monocytes. Through in vitro culture of such monocytes in the presence of the cytokines, granulocyte-monocyte colony stimulating factor (GM-CSF) and interleukin-4 (IL-4), one generates an immature myeloid DC that is characterized by its high capacity to take up materials (including foreign antigens) from its surroundings. When the immature DC receives an appropriate signal during this stage it is activated to migrate through the lymphatic vessels to the secondary lymph nodes. During this migration and upon reaching the lymph node it undergoes further changes that lead to a stage of full maturation. In the mature stage, the DC expresses high levels of MHC class I and class II molecules, which allow it to present antigens in the form of peptides derived from intracellular proteins to CD8-positive and CD4-positive T cells, respectively. The antigens that are presented by both types of MHC molecule and displayed on the surface of DCs are generated within the DC in a complicated cellular process that includes various steps of antigen processing and presentation. In the case of peptides (i.e. antigen-fragments) that are presented at the DC cell surface in MHC class I molecules it is necessary that the APC expresses molecules encoded by the transporter-associated with antigen processing (TAP) genes, TAP1 and TAP2.

The MHC-peptide ligands that are displayed at the DC surface interact with antigen-specific receptors present on T lymphocytes (i.e. T cell receptors). This interaction delivers the first signal (i.e. signal 1) to the T cell; because this signal is delivered through the TCR, which is unique for each T cell, it determines the antigen-specificity of the resultant response by selecting the T cells with fitting TCRs. Mature DCs also express a wide variety of costimulatory molecules, including CD40, CD80, CD86 to name a few, that interact with additional receptors expressed by T lymphocytes and cause their further activation (i.e. signal 2). Furthermore, DCs have the capacity to secrete a variety of soluble molecules, including cytokines and chemokines, which can attract different subtypes of lymphocytes to their vicinity and can impinge on the differentiation of the T cells receiving signal 1 and signal 2. Following binding to a further set of receptors expressed by lymphocytes these factors can deliver yet another signal to the lymphocytes which can influence their differentiation and ultimate function. This is sometimes referred to as signal 3.

It is possible to generate immature and mature DC in vitro. For example monocytes can be obtained by various procedures (positive selection of CD14-positive cells using commercial kits for cell selection, by their property of adherence to plasticware, or by their size and density using the process of cell elutriation). These monocytes are then cultured with GM-CSF and IL-4 to yield populations of immature DCs. Different combinations of reagents can be used to induce maturation of DCs and in parallel to alter their secretion of soluble mediators. These different forms of immature/mature DCs in turn can be used to activate T cells that not only have the desired antigen-specificity due to the interactions of their TCR with the MHC-peptide ligands displayed by the DC but also having desired functions based on the cytokines secreted by the DCs. Thus, mature DCs that are generated to secrete high amounts of the cytokine IL-12 have a good capacity to activate CD4 T cells of the T helper type 1 which are particularly important in anti-tumor immunity.

If properly activated and selected, T cells have the capacity to recognize and destroy tumor cells or cells infected with various pathogens. In the case of tumor cells, the tumor-associated antigens (TAA) that are processed and presented by APCs often represent molecules that are self-proteins that are overexpressed in tumor cells. Because most T cells that bear TCR that interact with MHC-peptide ligands derived from self molecules are eliminated in the thymus in a process known as "negative selection" there are few T cells in the repertoire that have TCR with sufficient avidity to recognize tumor cells expressing such TAA-ligands.

Figure 2:
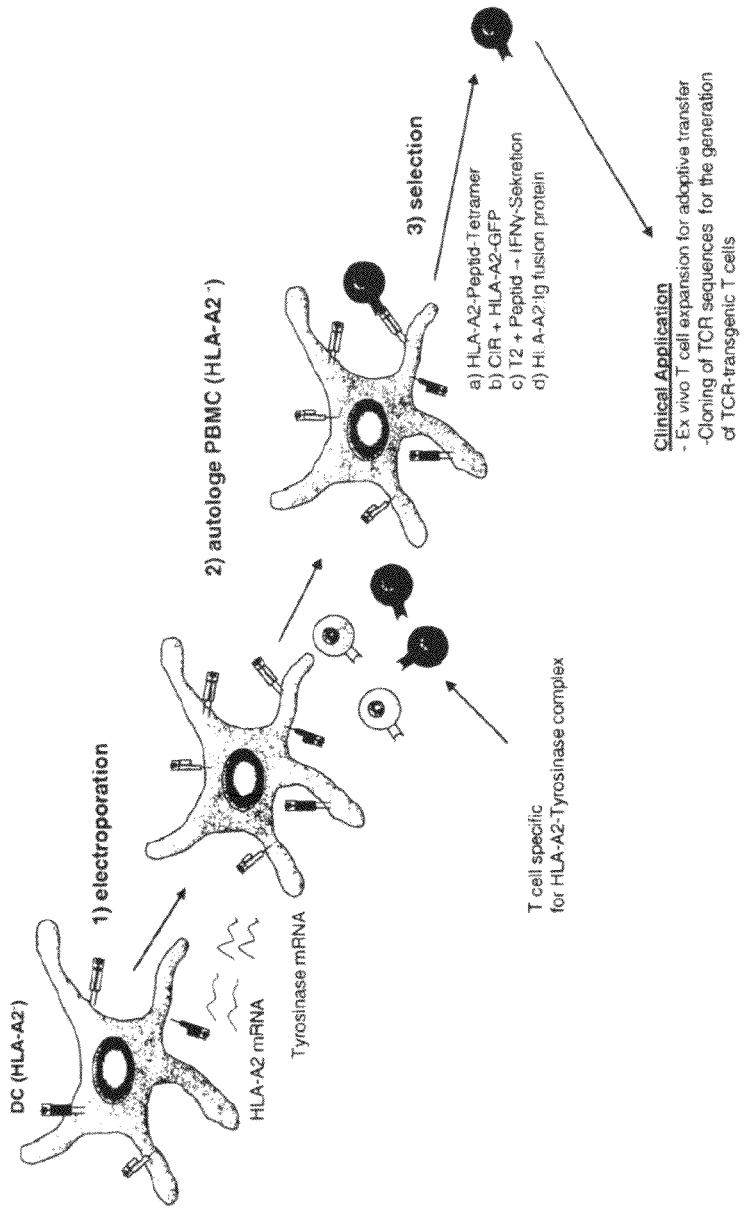
FIG. 2 is illustrating the de novo priming of naive tumor-specific T-cells with RNA-pulsed dendritic cells.

FIG. 2. De Novo Priming of Naïve Tumor-Specific T Cells with RNA-Pulsed Dendritic Cells In order to obtain T cells that have better capacity to recognize MHC-peptide ligands on tumor cells or other cells, such as those infected with pathogens, one can tap a non-selected repertoire of T cells from a healthy individual by presenting peptides derived from the selected antigen/antigens via allogeneic MHC molecules. For example, T cells from a healthy donor A, who is not HLA-A2, have not been exposed to HLA-A2-peptide complexes in the thymus, therefore there are T cells available among the peripheral blood mononuclear cells (PBMC) of such an individual that express TCR capable of interacting with HLA-A2-peptide complexes with high avidity. In order to stimulate naïve T cells bearing such desired TCR, DC of said donor A are generated from monocytes and are then modified to express an allogeneic MHC class I or class II molecule. Here an example is provided for HLA-A2. This molecule is an allogeneic MHC molecule for T cells of donor A, who is not HLA-A2. By introducing HLA-A2 encoding RNA into DCs of donor A, it is possible to create a population of DCs that express HLA-A2 molecules at their cell surface. Hereby, the DC still expresses its normal set of self-MHC molecules that are encoded by the chromosomal MHC genes of donor A, but in addition it expresses the allogeneic MHC molecule which is translated from the introduced RNA. At the same time the DC can be provided with RNA encoding a protein antigen from which peptides can be processed by the DC and presented at the cell surface by the allogeneic HLA-A2 molecule. When DCs expressing such allogeneic MHC-peptide ligands at their cell surface are used as APC to stimulate naïve T cells they can activate T cells with TCR that interact with the desired allogeneic MHC-peptide ligands. Not all T cells recognizing the allogeneic MHC molecules will have the desired peptide specificity, therefore the cells with the desired TCR must be selected from the full population of activated T cells. There are several procedures which are well known to immunologists to achieve this selection. For example, the activated T cells can be cloned as individual cells and following expansion, the T cell clones can be analyzed for their MHC-peptide specificity and those with the desired specificity can be selected for further use. Alternatively, soluble MHC-peptide ligands in various forms, such as tetramers, can be marked with a fluorescent label and incubated with the activated T cells. Those T cells bearing TCR that interact with the tetramers can then be detected by flow cytometry and sorted on the basis of their fluorescence.

The T cells that are selected with the desired TCR specificity may then be expanded in vitro for use in adoptive cell therapies (ACT) of patients whose tumors or infected cells express the corresponding HLA-A2-peptide ligands. Alternatively, the TCR sequences can be isolated and determined for such T cells and used to generate TCR constructs that can be introduced into lymphocytes or other cells to generate transgenic TCR cells that can be used for ACT.

Figure 3:
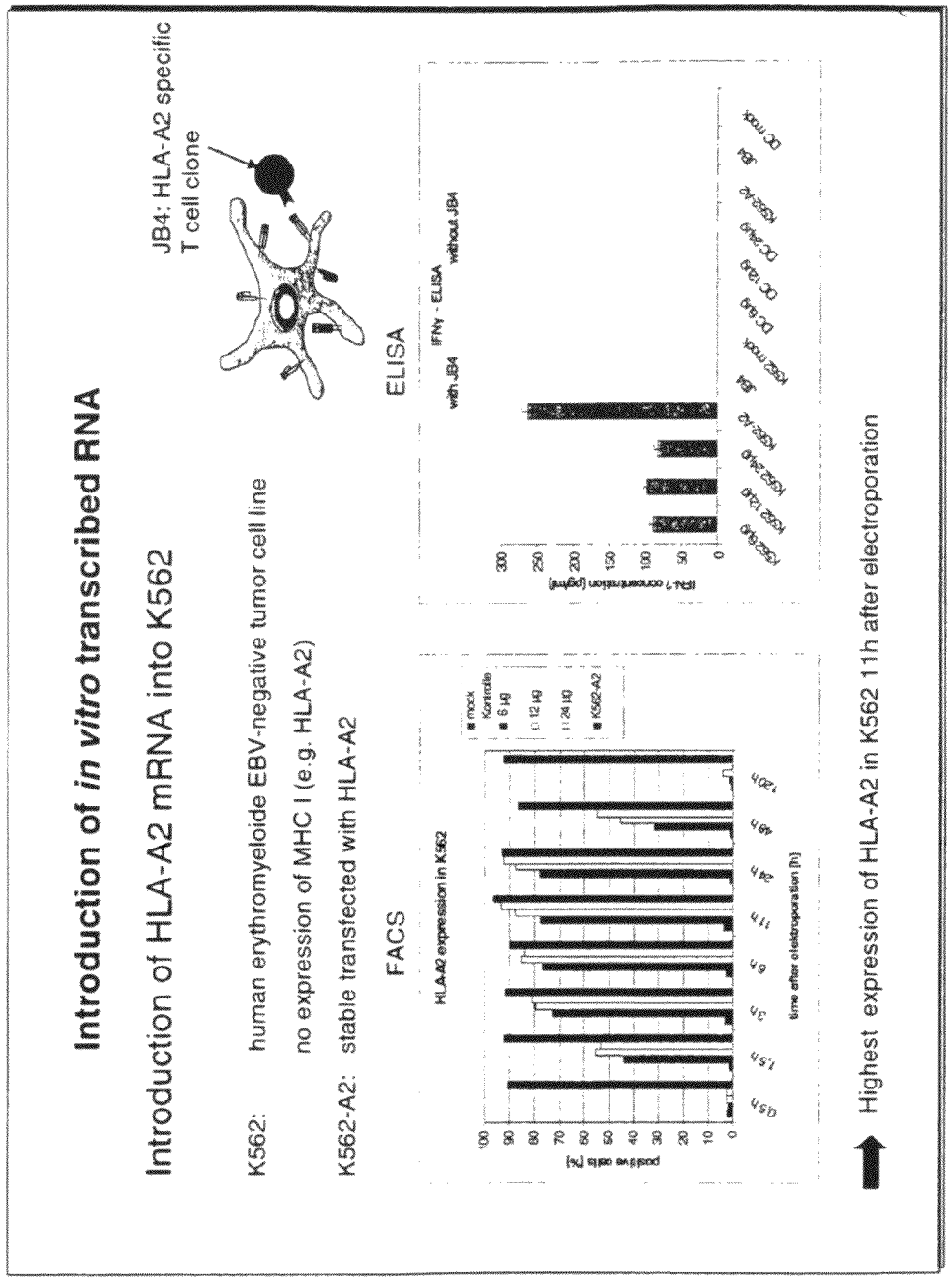
FIG. 3-9 are showing the introduction of in vitro transcribed RNA.

FIG. 3. Introduction of In Vitro Transcribed RNA into K562 Cells

As a first experimental approach to demonstrate the feasibility of this strategy we used the K562 cell line as a recipient cell line for expression of an allogeneic HLA-A2 MHC molecule following RNA transfer. This cell line is derived from an erythromyeloid leukaemia and is well known to cellular immunologists. Because it is a tumor line it can be grown to large numbers and is easy to handle experimentally. Furthermore, it does not express any MHC class I molecules on its cell surface therefore expression of allogeneic MHC molecules can be easily detected at the cell surface of K562, following introduction of nucleic acids encoding MHC class I molecules.

In the experiments summarized in this figure, HLA-A2 mRNA, which was generated by in vitro transcription from an HLA-A2-encoding cDNA, was introduced into K562 cells via electroporation. The transiently RNA-transfected cells were compared with a line of K562 cells that were stably transfected with the gene encoding HLA-A2, designated as K562-A2 cells.

The surface expression of HLA-A2 molecules was determined by flow cytometry following incubation of the cells with a monoclonal antibody specific for HLA-A2 molecules and the data are presented as percentages of positive cells (left hand figure). As a mock control the K562 cells were electroporated in a cuvette containing water instead of HLA-A2 mRNA. At all time points subsequent to electroporation, no positive cells were detected in the mock control. Three different amounts of HLA-A2 RNA were used for electroporation of the same number of K562 cells. The highest percentage of HLA-A2 positive cells was detected using the amount of 24 micrograms of RNA and the highest percentage of cells was seen at 11 h after electroporation. The percentages of positive cells expressing HLA-A2 molecules following electroporation of RNA were comparable at 11 h and 24 h to those of the positive control K562-A2 cells that stabily express the HLA-A2 gene. The transient expression of HLA-A2 following introduction of HLA-A2 mRNA is demonstrated by the decrease in percentages of positive cells at 48 h and no detection at 120 h.

To determine whether T cells bearing TCR that recognize HLA-A2 molecules as an alloantigen could be activated by HLA-A2 RNA-expressing cells, a T cell clone designated as JB4 was studied. This T cell clone secretes the cytokine interferon-gamma when its TCR interacts with HLA-A2-peptide ligands. The exact peptide/s required for this recognition is not known but is expressed in K562 cells and in DCs and in most other cells that we have tested, thus it appears to be derived from a ubiquitous protein. When JB4 cells are cocultured with K562 mock transfected cells, no IFN-gamma release is detected (right hand figure). Strong release is seen with the positive control of K562-A2 cells. All K562 cells transfected with various amounts of HLA-A2 RNA could induce secretion of cytokine by JB4 cells, albeit at lower levels than the positive control. Nevertheless, these are substantial levels of cytokine release. In cultures of K562 or DCs that did not have addition of JB4 cells, no cytokine release was measured, demonstrating that the stimulating cells do not secrete interferon-gamma themselves. A final control of JB4 cells without stimulating cells showed no cytokine release and demonstrated that the T cells must be activated by the appropriate MHC-peptide ligand to secrete interferon-gamma.

These studies showed that introduction of an allogeneic MHC molecule into K652 cells via transient RNA expression led to cell surface expression of HLA-A2 molecules and the cells could activate an HLA-A2 alloantigen-specific T cell clone.

Figure 4:
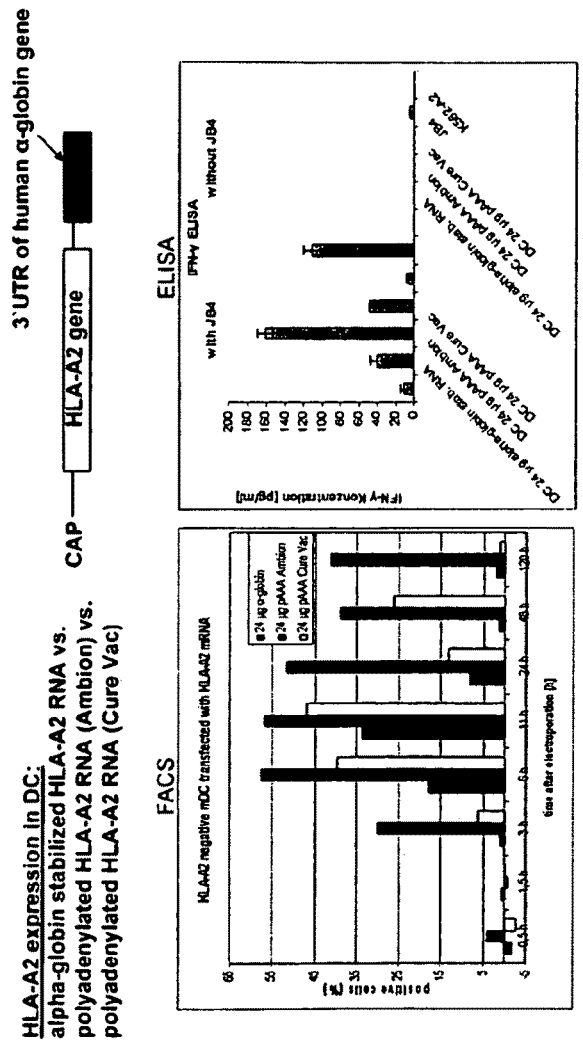

FIG. 4. Introduction of In Vitro Transcribed RNA into DCs.

A similar experimental approach was used as described in FIG. 3 to assess surface expression of HLA-A2 molecules on DCs following electroporation of HLA-A2 mRNA and to assess their capacity to stimulate cytokine secretion from JB4 cells. Here an amount of 24 micrograms of HLA-A2 mRNA was used throughout but three different sources of mRNA were compared. These included a commercial source of in vitro transcribed RNA in which the 3' UTR of the human alpha-globulin gene was added to the HLA-A2 gene contruct, with the intention to stablize the RNA expression inside the DCs. This RNA was compared to polyadenylated HLA-A2 RNA generated using a commercial procedure and kit from Ambion versus a similar RNA generated using a commercial procedure and kit from CureVac. The polyadenylated mRNA generated using the Ambion procedure and introduced by electroporation into DCs cultured from an HLA-A2 negative donor showed the best results. The highest percentages of HLA-A2 positive cells were found with this mRNA, the appearance of HLA-A2 molecules at the surface of the DCs was detected earlier (at 6 h) and expression in the DCs was still found at 120 h using this source of mRNA. All further experiments therefore utilized this source of mRNA.

The DCs were studied for their capacity to stimulate cytokine secretion from JB4 cells as described in FIG. 3. Mock control DCs (most left column) induced only background levels of cytokine release. Higher levels were seen using DCs expressing the three different sources of mRNA but those DCs electroporated with Ambion mRNA were superior. The DC cultures containing no JB4 cells did not have interferon-gamma, demonstrating that it is only released by the JB4 cells following stimulation with HLA-A2-RNA expressing DCs.

Figure 5:
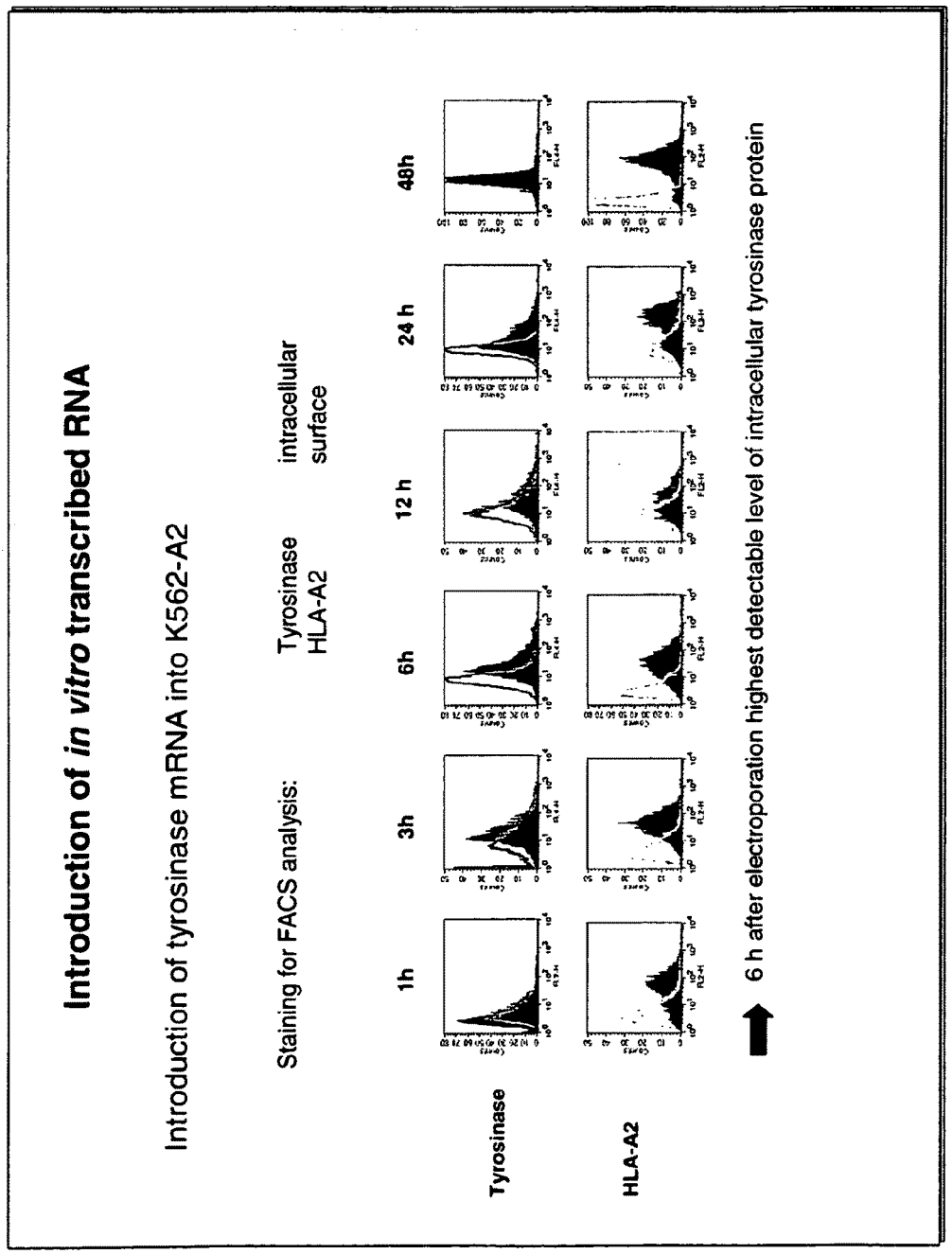

FIG. 5. Introduction of In Vitro Transcribed RNA Encoding the Tumor-Associated Antigen Tyrosinase into K562-A2 Cells.

RNA was generated using the Ambion procedure and specific for the antigen tyrosinase. It was electroporated into K562-A2 cells and surface expression of HLA-A2 was measured using a monoclonal antibody specific for HLA-A2 molecules. The green curves represent staining with an isotype control antibody and the blue curves staining with the HLA-A2-specific antibody. Here HLA-A2 surface expression was found at all time points since K562-A2 cells constitutively express the HLA-A2 gene. A decrease in expression of HLA-A2 was noted at 12 h which may be related to a stress-induced impact as a result of electroporation. The cells recovered high expression of HLA-A2 molecules thereafter. Protein expression of tyrosinase was measured following intracellular detection of protein using a monoclonal antibody specific for tyrosinase. The orange curves represent the staining of the mock control and the blue curves represent the tyrosinase protein inside the cells. A slight shift in staining could be seen at several time points indicating that protein was being made following introduction of the tyrosinase RNA.

Figure 6:
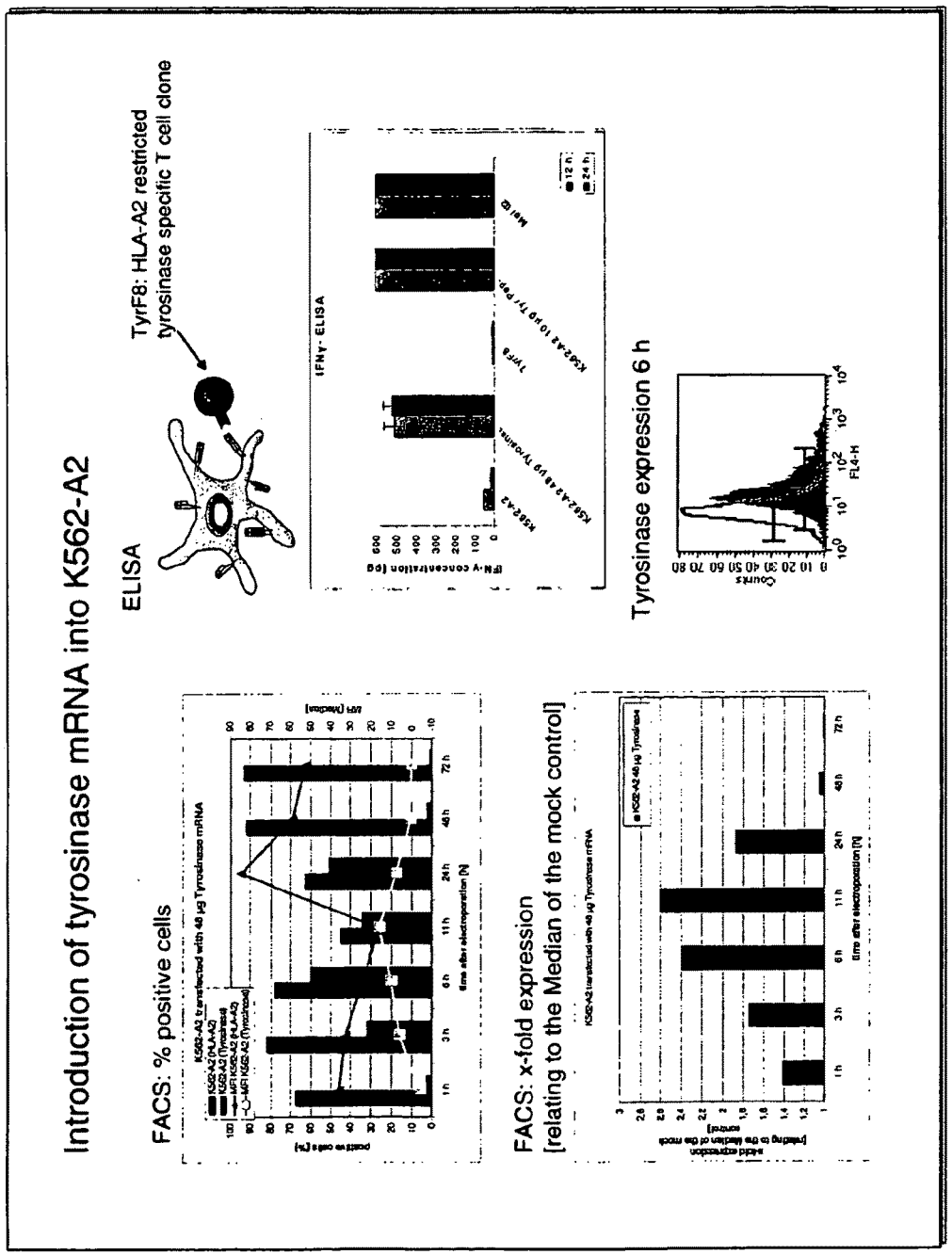

FIG. 6. Expression and Function of Tyrosinase in K562-A2 Cells

Tyrosinase RNA was electroporated into K562-A2 cells and the percentages of positive cells as well as the intensity of staining, designated as mean fluorescent intensity (MFI), was determined at various time points (upper left field). The red columns show the constitutive HLA-A2 expression on K562-A2 cells, again with a drop in level between 11 and 24 h and recovery thereafter. The blue columns show the intracellular staining of tyrosinase protein with the peak at 6 h. The shift in staining at 6 h is illustrated in the lower right field in which the mock control staining is shown by the orange curve and the tyrosinase staining shown by the blue curve. The fold increase in expression compared to the mock control, over time, is shown in the lower left field, giving a maximum at 11 h. The interferon-gamma secretion of a T cell clone, Tyr-F8, which sees a tyrosinase-derived peptide presented by HLA-A2 molecules is shown in the upper right field. K562-A2 cells do not induce interferon-gamma secretion by Tyr-F8 T cells, but they do so following electroporation with tryosinase RNA. The T cells alone do not secrete cytokine but they can also be stimulated by K562-A2 cells loaded with synthetic peptide from tyrosinase or by melanoma cells that co-express tyrosinase and HLA-A2 (MEL-IL2 cells).

This demonstrates that introduction of RNA for tyrosinase into K562-A2 cells allows them to process and present the appropriate MHC-peptide ligand that is seen by the TCR of Tyr-F8 cells and activates the T cells to secrete interferon-gamma. RNA transfected cells used 12 and 24 h after electroporation had comparable stimulatory capacities.

Figure 7:
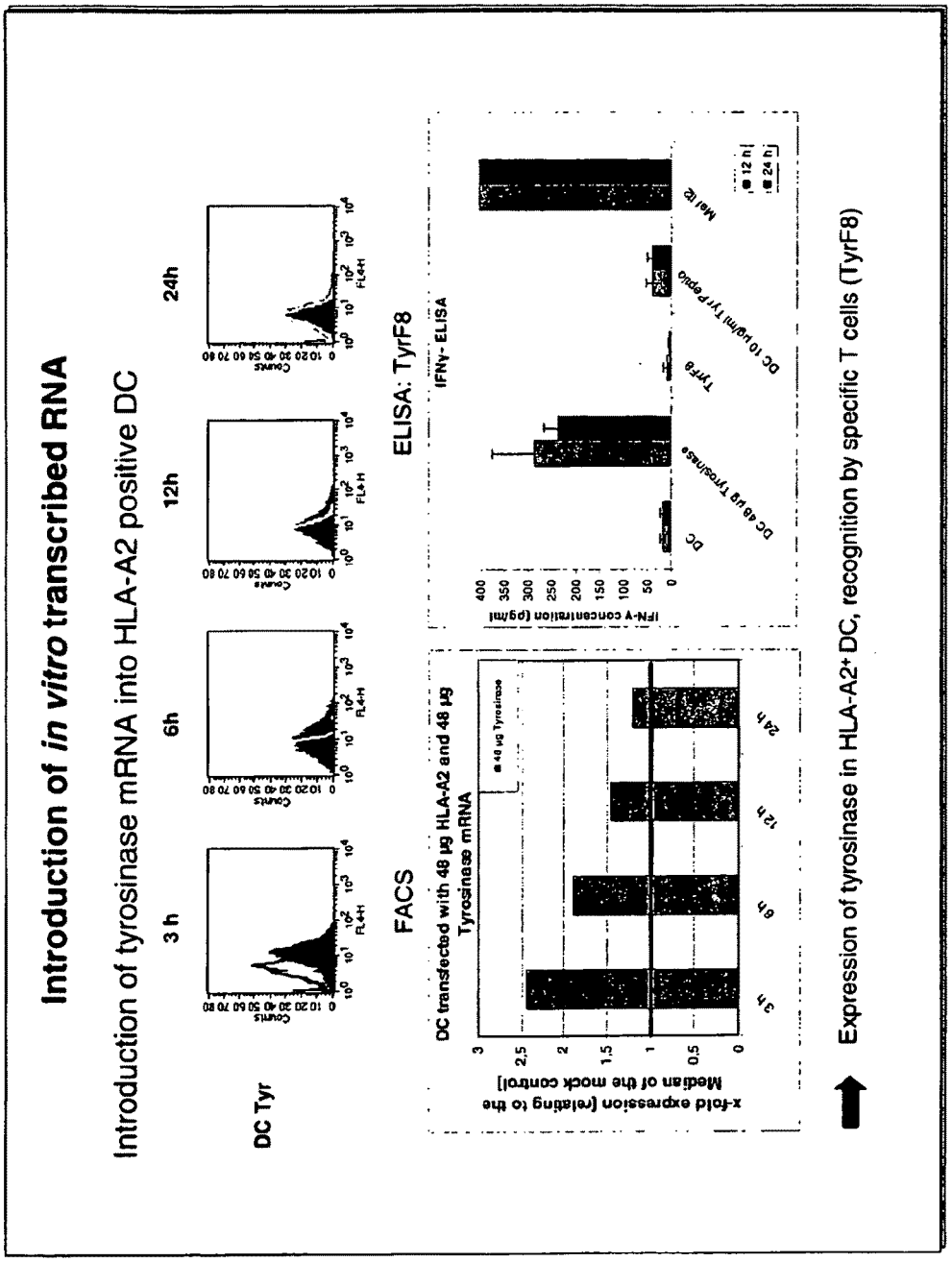

FIG. 7. Introduction of In Vitro Transcribed Tyrosinase RNA in DCs Generated from HLA-A2 Positive Donors.

A similar set of experiments was done as those described in FIG. 6 except DCs from an HLA-A2-positive donor were used instead of K562-A2 cells. Expression of intracellular tyrosinase protein was detected in the DCs at various time points following electroporation of RNA (upper panels). The highest mean fold expression over the mock control was seen at 3 h in the DCs. DCs alone could not stimulate cytokine secretion by TyrF8 cells but they could do so following electroporation with tyrosinase RNA. DCs used either 12 h or 24 h after electroporation had the capacity to activate Tyr-F8 T cells to secrete interferon-gamma.

Figure 8:
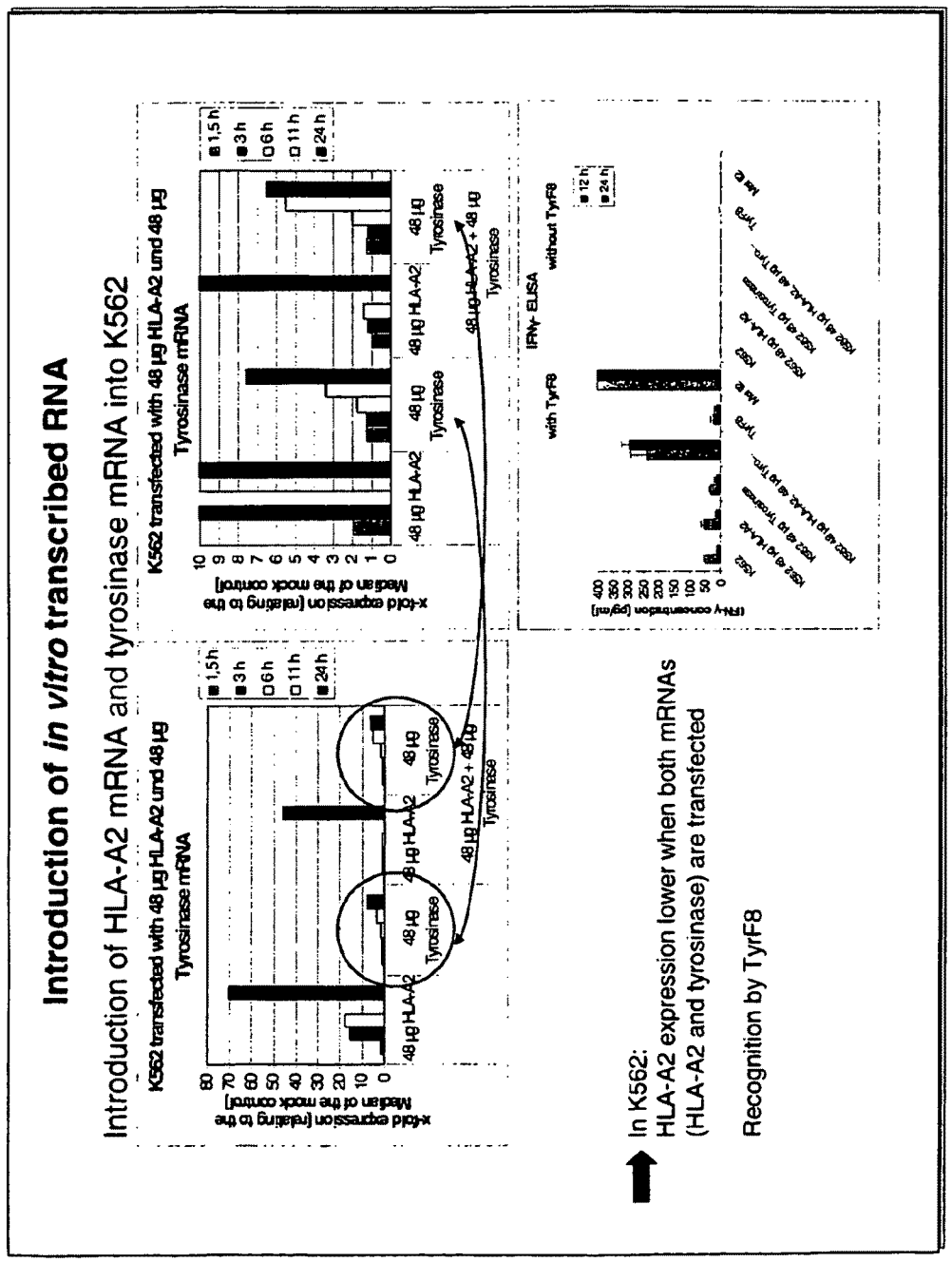

FIG. 8. Co-Expression of HLA-A2 and Tyrosinase in K562 Cells.

K562 cells which do not express any HLA molecules were electroporated with RNA for HLA-A2 and tyrosinase. Either each species of RNA was introduced individually or both in combination. The upper right panel summarizes the protein expression of HLA-A2 alone at different time points (most left set of columns) tyrosinase alone, followed by HLA-A2 staining in cells electroporated with both HLA-A2 and tyosinase RNA and the tyrosinase staining in cells receiving both species of RNA. Optimal expression of both proteins in cells electroporated with both species of RNA was seen at 24 h. The K562 cells co-expressing both RNAs could stimulate interferon-gamma secretion from TyrF8 cells 12 h and 24 h after electroporation.

Figure 9:
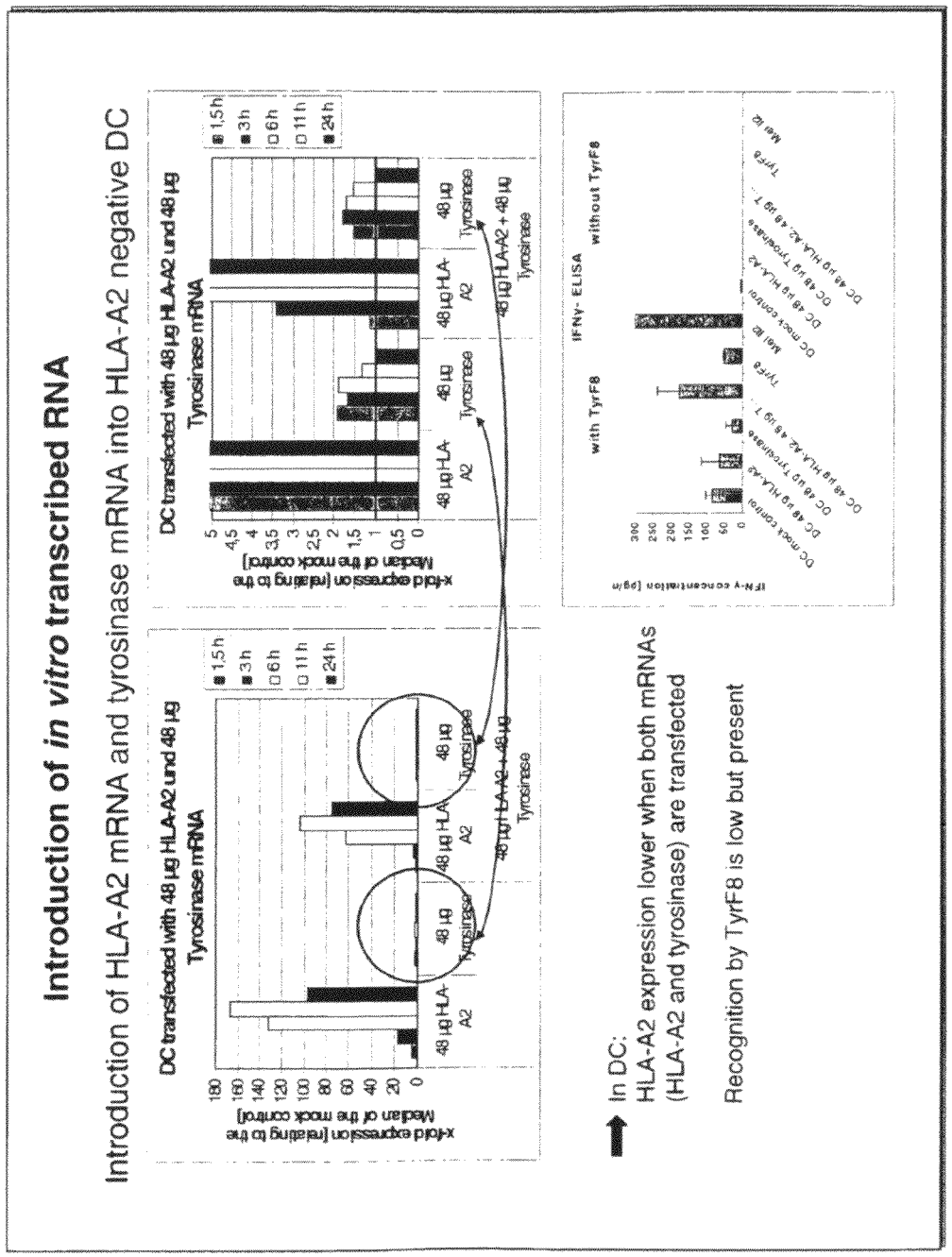

FIG. 9. Co-Expression of HLA-A2 and Tyrosinase in DCs Made from HLA-A2 Negative Donors.

Co-expression of HLA-A2 protein and tyrosinase protein in DCs prepared from an HLA-A2 negative donor was analyzed as described in FIG. 8. Co-expression of both proteins was found in DCs at various time points. The levels of HLA-A2 expression seemed to be reduced in the presence of tyrosinase RNA. Nevertheless the DCs co-expressing both RNAs could stimulate significant levels of interferon-gamma by TyrF8 cells above those of the T cells alone or following incubation with DCs electroporated with the single species of RNA.

Figure 10:
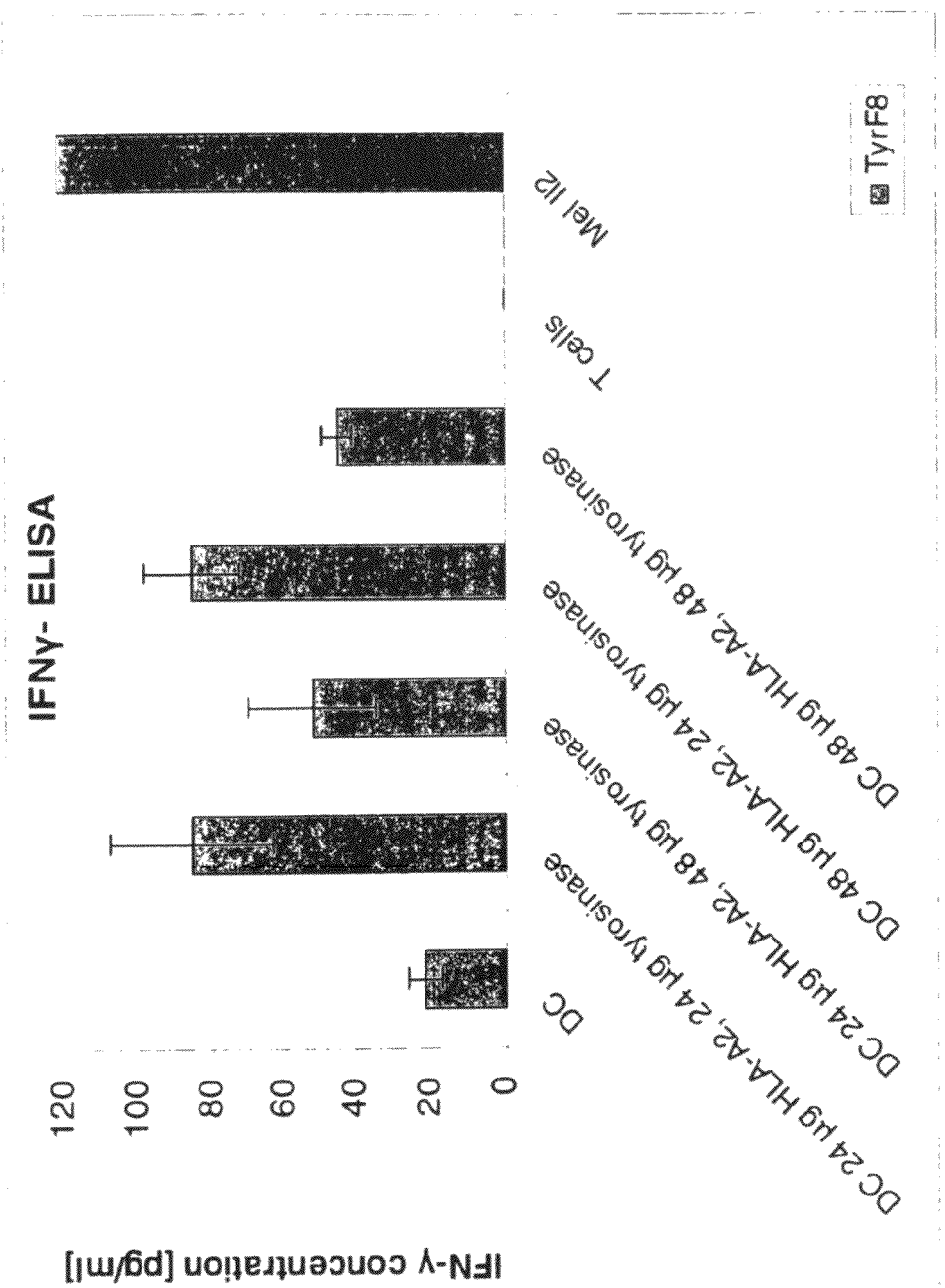
FIG. 10 is showing the influence of RNA concentration of restimulation of TyrF8 cells by RNA-expressing DCs.

FIG. 10. Influence of RNA Concentration of Restimulation of TyrF8 Cells by RNA-Expressing DCs.

The capacity of DCs to stimulate cytokine secretion from TyrF8 cells was analyzed using DCs prepared from an HLA-A2 negative donor transfected with different amounts of HLA-A2 and tyrosinase RNA. Mock control DCs (most left column) induced only background levels of cytokine release. The T cells alone do not secrete cytokine but they can also be stimulated by melanoma cells that co-express tyrosinase and HLA-A2 (MEL-IL2 cells).

All DCs transfected with various amounts of both RNAs could induce secretion of interferon-gamma by TyrF8 cells, whereas those DCs electroporated with 24 µg HLA-A2 and 24 µg tyrosinase RNA or 48 µg RNA HLA-A2 and 24 µg tyrosinase RNA were superior indicating that less RNA for the restimulation of T cells may be better.

Figure 11:
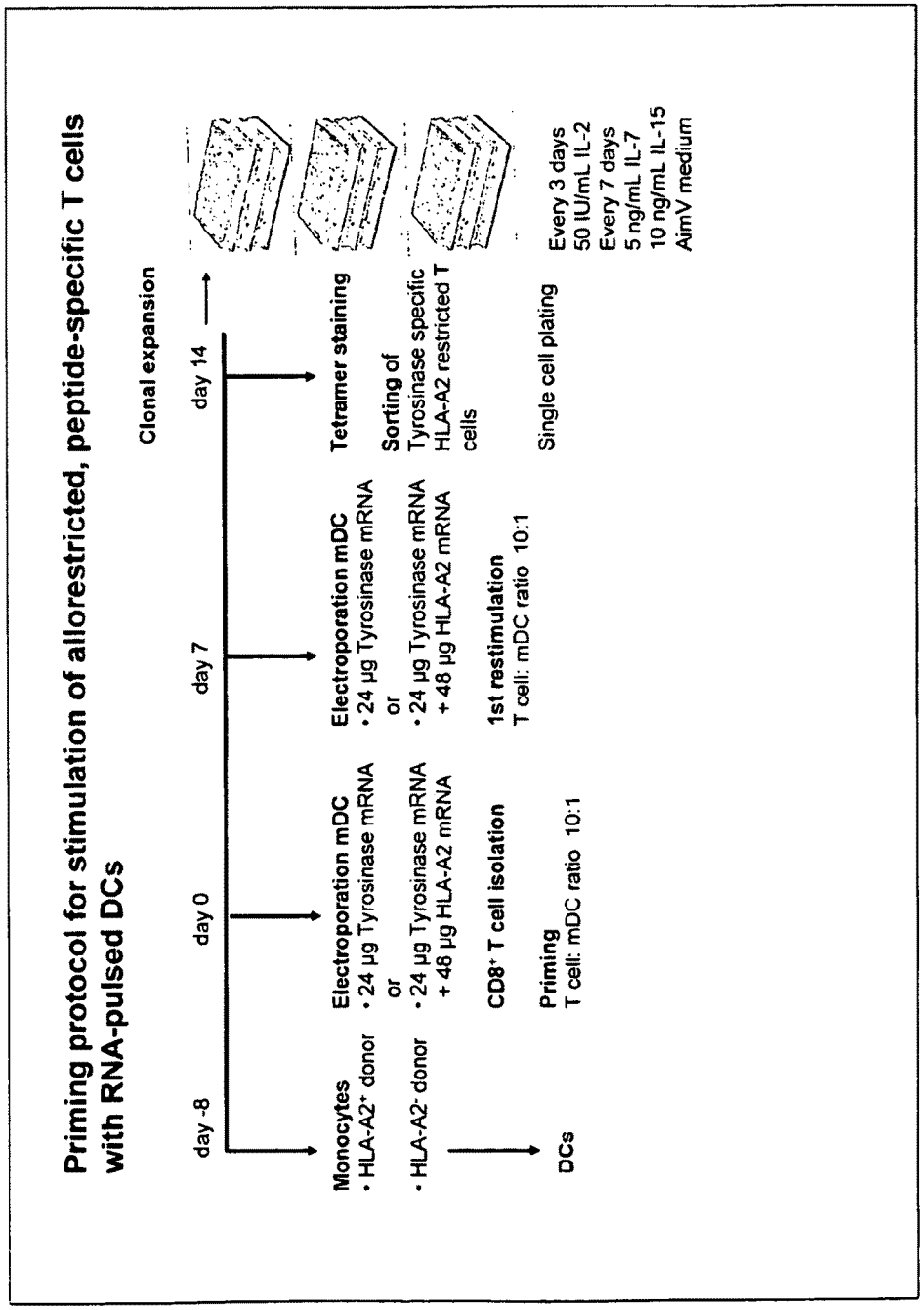
FIG. 11 illustrates the de novo priming protocol of naïve T cells with RNA-pulsed dendritic cells.

FIG. 11. De Novo Priming Protocol of Naïve T Cells with RNA-Pulsed Dendritic Cells In order to analyze the capacity of RNA-loaded DCs to prime naïve T cells to become tumor-specific lymphocytes, a three phase priming protocol was developed. Eight days in advance of the initiation of priming (day-8), monocytes were prepared by plastic adherence from an HLA-A2-positive donor and an HLA-A2-negative donor, as described. These purified monocyte populations were used to prepare immature DCs that were then matured as described. On the first day (day 0) of the T cell priming protocol the DCs were loaded with RNA via electroporation, as described. The DCs derived from the HLA-A2-positive donor were loaded with 24 µg of tyrosinase RNA as a model tumor antigen. Tyrosinase protein translated from the RNA in the DCs should be processed and presented as peptides in association with the self-encoded HLA-A2 molecules at the DC surface. The DCs derived from the HLA-A2-negative donor were loaded with RNA encoding HLA-A2 (48 µg) and tyrosinase (24 µg). Here the HLA-A2 molecules encoded by the transferred RNA represent allogeneic MHC molecules. Peptides derived from the tyrosinase protein should be processed and presented by HLA-A2 molecules that are translated from the HLA-A2 encoding RNA transferred to the DCs; these peptide-MHC complexes represent allorestricted-peptide ligands. On day 0 of the priming protocol, autologous CD8+ T lymphocytes from each donor were isolated via negative selection using a commercial kit and the manufacturer's instructions (CD8+ T cell Isolation Kit II (human), Miltenyi, Bergisch Gladbach, Germany) to >80% purity. These untouched autologous CD8+ T cells were added to the mature RNA-pulsed DCs 9 h after electroporation at a ratio of 10:1 in AimV medium (Gibco BRL, Karlsruhe, Germany) containing IL-7 (10 ng/mL). IL-2 (20 IU/mL) was added after 2 days and then on every $3^{rd}$ subsequent day. Seven days (day 7) after the $1^{st}$ stimulation, the $2^{nd}$ stimulation of the priming cultures was performed using RNA-pulsed DCs prepared in the same manner as for the $1^{st}$ stimulation and using the same culture conditions as used on day 0 of priming. After an additional 7 days (day 14), HLA-A2-restricted tyrosinase-specific T cells were sorted with the aid of a phycoerythrin (PE)-labeled HLA-A*0201/htyr369-377peptide/human $\beta_2$m tetramer (Wölfl et al., 2004; provided by Prof. D. Busch, Institute of Medical Microbiology, Immunology and Hygiene, Technical University, Munich, Germany). Some of the positively-selected T cells were plated at 1 cell/well in 96-well V-bottomed plates (TPP, Trasadingen, Switzerland). The wells were fed with Aim V medium containing 50 IU/mL IL-2 (Chiron Behring, Marburg, Germany) every three days and 5 ng/mL IL-7 (Promokine, Heidelberg, Germany) and 10 ng/mL IL-15 (PeproTech Inc., New Jersey, United States) every seven days. Selected clones and the remaining tetramer-selected uncloned T cells were maintained in culture in Aim V medium, with IL-2, IL-7, IL-15, as above, and were provided with feeder cells, comprised of peripheral blood mononuclear cells derived from a pool of five donors which was irradiated with 50 Gy. The T cells were stimulated non-specifically with anti-CD3 antibody (0.1 µg/mL; provided by Dr. Elisabeth Kremmer, Institute of Molecular Immunology, GSF, Munich, Germany) every two weeks.

Figure 12:
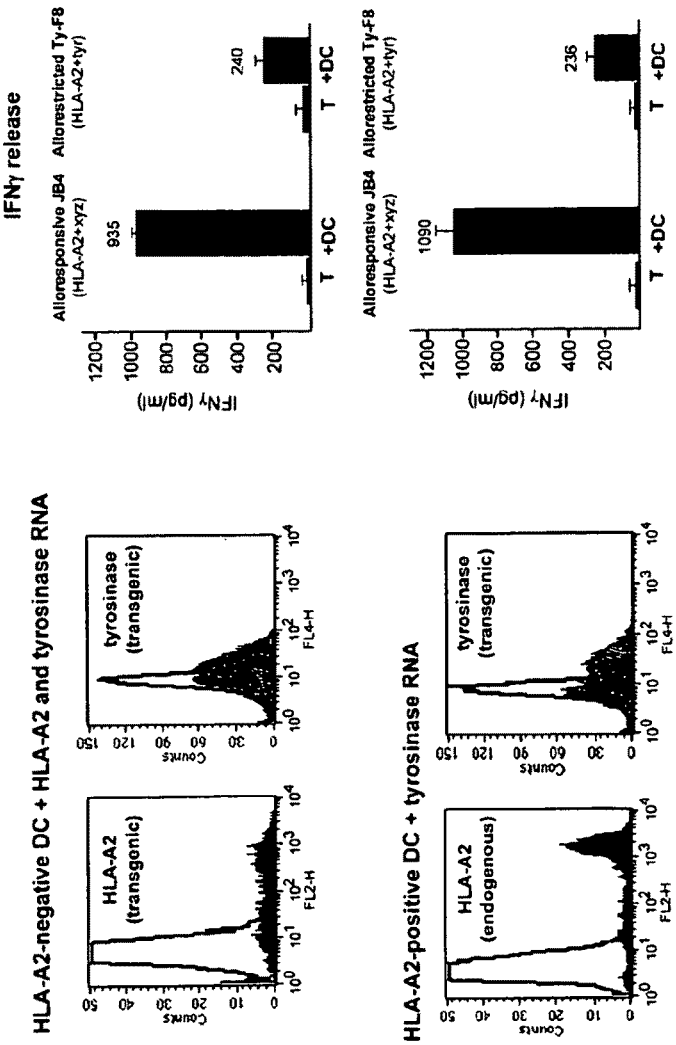
FIG. 12 shows the expression of MHC-peptide ligands on RNA-transfected dendritic cells.

FIG. 12. Expression of MHC-Peptide Ligands on RNA-Transfected Dendritic Cells

To demonstrate that the DCs used for T cell priming expressed the expected MHC-peptide ligands, the expression of HLA-A2 molecules at the cell surface and intracellular tyrosinase protein was determined using flow cytometry as described previously. Co-expression of HLA-A2 molecules and tyrosinase protein was detected at high levels in DCs derived from both donors. The levels of intracellular tyrosinase protein were comparable in the DCs prepared from both the HLA-A2-positive and the HLA-A2-negative donor. The levels of HLA-A2 surface expression on a majority of cells were higher in the DCs prepared from the HLA-A2-positive donor where they are encoded by an endogenous gene. Whereas the levels of transgenic HLA-A2 molecules are more variable on the DCs prepared from the HLA-A2-negative donor.

The capacity of such DCs, using cells prepared according to the same protocol in independent experiments, to stimulate T cells was determined using an HLA-A2-alloresponsive T cell clone that recognizes HLA-A2 molecules irrespective of the peptides they carry (i.e. HLA-A2+xyz peptides). Both populations of DCs were able to stimulate this T cell clone (JB4) to secrete interferon-gamma, as measured in a standard ELISA as described previously. No cytokine release was seen from T cells incubated without DCs. The presence of ligands comprised of HLA-A2 molecules presenting a tyrosinase-derived peptide, was assessed by measuring interferon-gamma release by a T cell clone (Tyr-F8) specific for HLA-A2-tyrosinase peptide. T cells incubated without DCs released only background levels of cytokine. In this experiment the HLA-A2-positive DCs were provided with 48 µg of tyrosinase whereas the HLA-A2-negative DCs were provided with 24 µg of tyrosinase.

These results demonstrated that the transgenic HLA-A2 molecules, provided by RNA transfer into the DCs derived from the HLA-A2-negative donor, could be stained at the cell surface with specific HLA-A2 antibody and recognized by an HLA-allospecific T cell clone (J84). The transfer of tyrosinase RNA led to intracellular protein expression in both DC populations. The co-transfer of HLA-A2 and tyrosinase RNA allowed an HLA-A2-tyrosinase specific T cell clone (Tyr F8) to be activated, as did the transfer of tyrosinase RNA into DCs expressing endogenously encoded HLA-A2 molecules.

Figure 13:
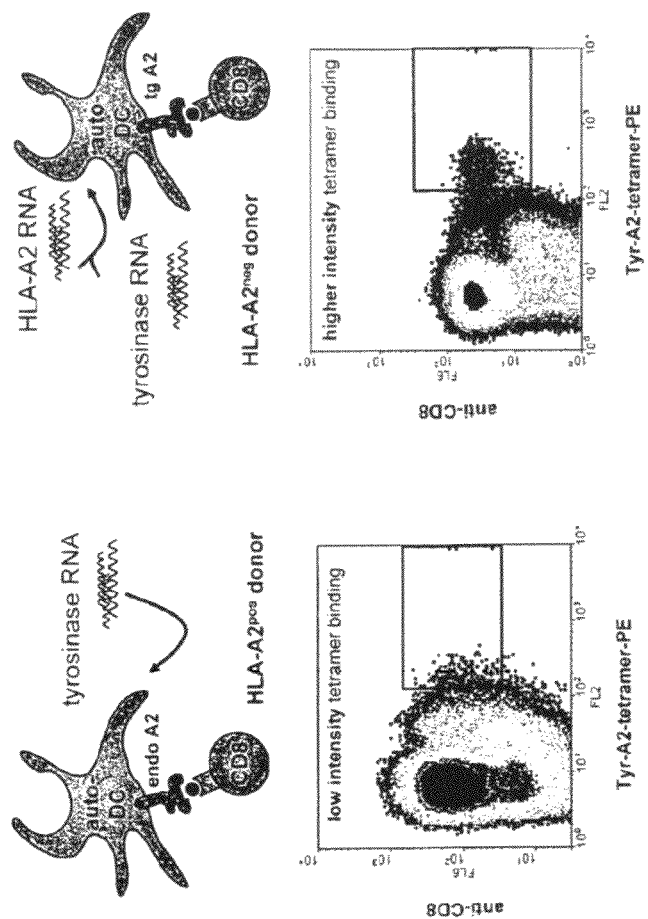
FIG. 13 depicts the tetramer staining of primed T cells from HLA-A2-positive and HLA-A2-negative donors.

FIG. 13. Tetramer Staining of Primed T Cells from HLA-A2-Positive and HLA-A2-Negative Donors To select T cells bearing T cell receptors specific for HLA-A2-tyrosinase peptide ligands that are present among the primed T cell cultures, the T cells were stained with an HLA-A*0201/htyr369-377/H$\beta_2$m tetramer and analyzed by flow cytometry. Cells from each of the two different priming cultures that showed tetramer binding were gated (black rectangle, □) and isolated in a MoFlo™ High-Performance Cell Sorter (Dako, Fort Collins, Colo., USA). The CD8+tetramer+ T cell population of the HLA-A2-positive donor showed tetramer binding at only a low intensity whereas the CD8+ tetramer+ cells from the HLA-A2-negative donor were stained at a higher intensity. The sorted tetramer T cells were plated as single cell and the remaining cells retained in culture as uncloned bulk cultures.

These results demonstrated that the priming protocol yielded T cells that carried TCR capable of binding HLA-A2-tyrosinase-specific tetramers. More T cells bound the tetramer at higher intensity in the cultures primed using the DCs derived from the HLA-A2-negative donor, indicating better stimulation by HLA-A2 allogeneic, peptide ligands.

Figure 14:
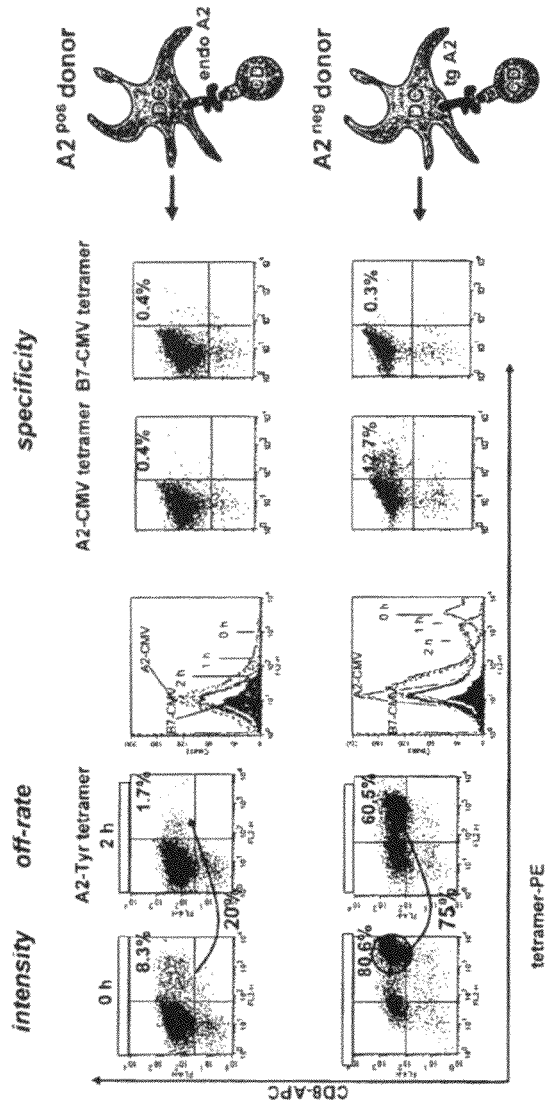
FIG. 14 shows the assessment of tetramer-sorted bulk T cell cultures for specificity and T cell receptor avidity.

FIG. 14. Assessment of Tetramer-Sorted Bulk T Cell Cultures for Specificity and T Cell Receptor Avidity The sorted cells that were retained as bulk cultures were reanalyzed for tetramer staining after 8 days. As expected, the majority of sorted cells were CD8+ in the sorted bulk cultures derived from both of the priming cultures. Tetramer+ T cells were present at a frequency of about 8% in the cultures primed using HLA-A2-positive DCs. These cells had an intermediate intensity of tetramer binding (MFI=127.49), whereas 80% of the bulk culture T cells from the HLA-A2-negative donor bound the tetramer with a much higher intensity (MFI=3248.77). The intensity of tetramer binding is one parameter used to assess T cell receptor (TCR) avidity for a particular MHC-peptide ligand (Yee et al., 1999). A higher intensity of tetramer binding indicates a better interaction of the ligand with the TCR. A second parameter of TCR avidity is the tetramer off-rate (Palermo et al., 2005). T cells are incubated with tetramer and are then washed and incubated in the absence of tetramer and the presence of antibody specific for HLA-A2 molecules. The presence of this antibody prevents tetramers which have fallen off the surface of the T cells from rebinding to the cell surface. The intensity of tetramer staining on the T cells is determined at various time points after washing: 0 h, 1 h, 2 h. If the tetramer staining is rapidly lost, this indicates that the TCR has only low avidity for the MHC-peptide ligand of the tetramer. If tetramer binding is more stable over time, this indicates a higher TCR avidity for the MHC-peptide ligand. In the comparison of the two bulk cultures, it was found that only 20% of the original tetramer-binding cells (1.7% vs 8.3%) were still tetramer after 2 h in the cells derived from the HLA-A2-positive donor. In contrast, 75% of the cells were still tetramer after 2 h in the T cells derived from the HLA-A2-negative donor (60.5% vs 80.6%).

The specificity of tetramer binding was determined using a tetramer comprised of HLA-B7 molecules presenting a peptide derived from cytomegalovirus (B7-CMV tetramer, provided by Prof. D. Busch). Both bulk T cell cultures showed only low levels of staining (0.3-0.4%).

In addition, an HLA-A2-CMV peptide tetramer was also used. Only 0.4% of T cells from the HLA-A2-positive donor bound this tetramer, whereas 12.7% of the bulk T cells from the second donor were positive. These T cells likely represent T cells with TCR that recognize HLA-A2 molecules as alloantigens, irrespective of the peptides they present. The intensity of tetramer binding was lower (MFI=166.98) compared to the intensity of the HLA-A2-tyrosinase-tetramer binding (MFI=3248.77).

These results demonstrate that T cells bearing TCR with higher avidity as defined by intensity of tetramer staining and slower tetramer off-rate were derived from the cultures using HLA-A2-negative DCs, demonstrating the superiority of inducing responses in non-negatively selected T cell repertoires, using allogeneic-peptide ligands.

Figure 15:
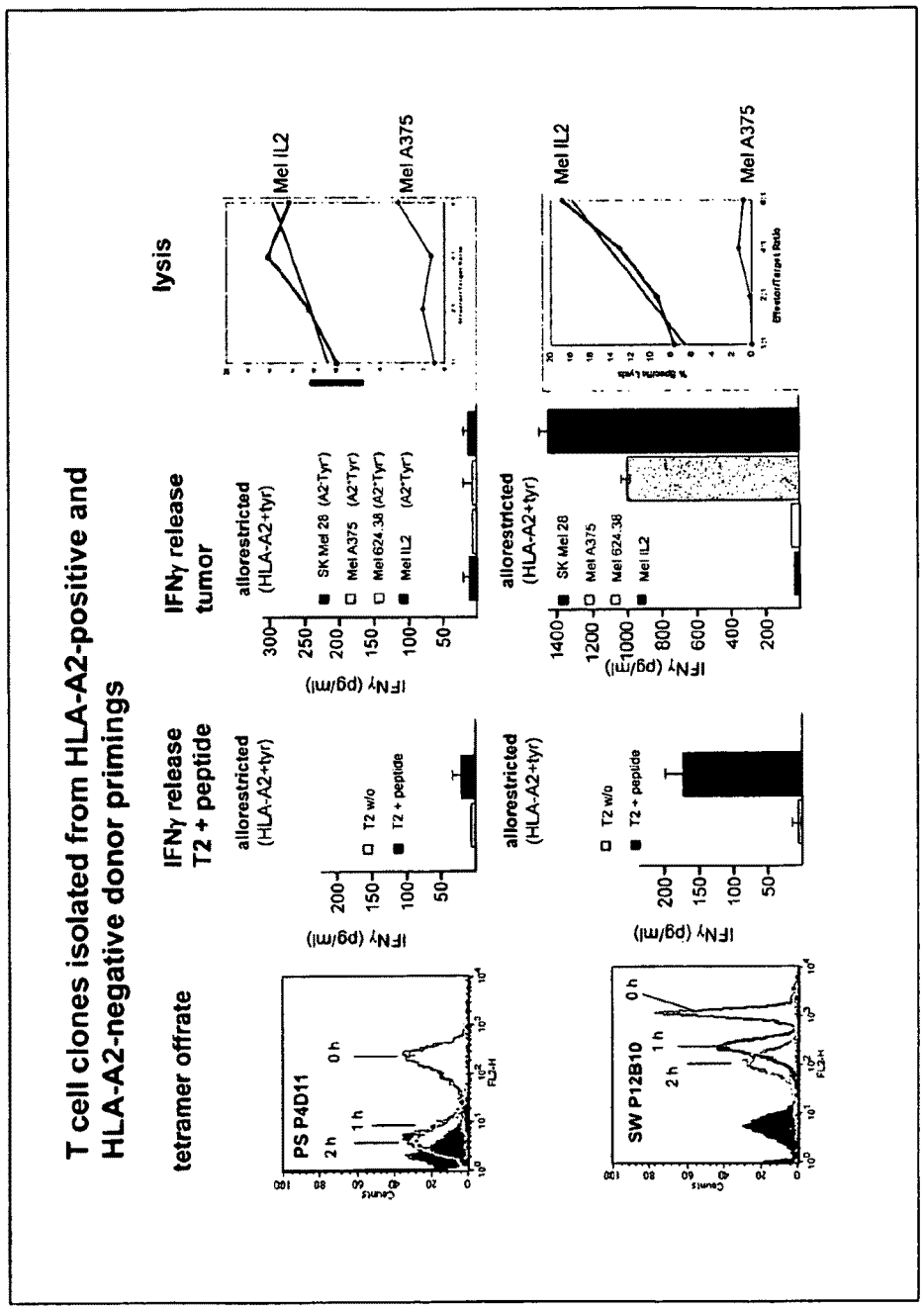
FIG. 15 depicts the assessment of T cell clones for specificity, T cell receptor avidity and function.

FIG. 15. Assessment of T Cell Clones for Specificity, T Cell Receptor Avidity and Function From the single cell plating experiments, two clones were selected for further characterization. One clone (PS P4D11) was derived from the HLA-A2-positive donor and one clone (SW P12B10) was derived from the HLA-A2-negative donor.

The PS P4D11 clone, from the HLA-A2-positive donor, showed an intermediate intensity of tetramer staining (MFI=166.98) with a rapid release of tetramer as measured at 1 h and 2 h. This T cell clone could not be stimulated to secrete interferon-gamma following incubation with T2 cells loaded with specific peptide (T2 cells provided by Peter Cresswell, Yale University, New Haven, Conn.) nor following stimulation with tumor cells, expressing HLA-A2 and tyrosinase (Mel 624.38 and Mel IL-2). It could, however kill HLA-A2$^+$tyrosinase$^+$ melanoma tumor cells but not HLA-A2$^+$tyrosinase$^-$ tumor cells, demonstrating its specificity for HLA-A2-tyrosinase ligands.

The SW P12B10 clone, derived from the HLA-A2-negative donor, showed a higher intensity of tetramer binding (MFI=1009.04) and the stability of tetramer binding was higher with all of the cells still positive for tetramer after 2 h. This clone showed specific interferon-gamma release following stimulation with T2 cells loaded with tyrosinase-derived peptide, but not against T2 cells without peptide, demonstrating peptide specificity. It also could be stimulated to release interferon-gamma following stimulation with HLA-A2$^+$tyrosinase$^+$ melanoma tumor cells, but not against HLA-A2-negative, tyrosinase positive melanoma cells (SK Mel 28) or against HLA-A2-positive, tyrosinase negative melanoma tumor cells (Mel A375). This pattern demonstrated that the clone was specific for an HLA-A2-tyrosinase peptide. This clone could also kill HLA-A2-positive, tyrosinase positive melanoma tumor cells, but not HLA-A2-positive, tyrosinase negative tumor cells.

These results show that the T cell clones derived from the two different priming cultures showed differences with respect to TCR avidity, as detected by intensity of tetramer binding and tetramer off-rate, with the allorestricted peptide-specific T cell clone having TCR of higher avidity by this definition. Furthermore, this T cell clone showed functional superiority since it could not only kill melanoma cells specifically, but could also be activated to secrete interferon-gamma following peptide stimulation and following stimulation with tumor cells, in an HLA-A2, tyrosinase-specific manner.

Materials and Methods

Adherent Tumour Cell Lines, Mel A375, Mel IL-2, Mel 624.38 and SK Mel 28

These human melanoma cell lines were cultured in RPMI 1640 medium supplemented with 12% fetal bovine serum, 1× Non-essential amino acids, 2 mM L-glutamine and 1 mM sodium-pyruvate. Volume of the medium in a middle-sized culture flask was 10 mL. Approximately every 3-4 days cells grew to confluence. Depending on the growth rate of individual cell lines they were split 1:2 to 1:10. The medium was removed, cells were washed once with PBS and then incubated with 2 mL trypsin/EDTA 2× for 3 min at room temperature. Detached cells were resuspended in fresh RPMI 1640 medium plus supplements.

T Cell Clones, JB4 and Tyr-F8

T cell clones were first expanded in standard restimulation cultures. Large stocks were aliquoted and frozen. Each time they were needed for an experiment, T cells were taken from the stock, thawed, placed into wells of a 24-well plate and restimulated according to standardised protocols.

Suspension Tumour Cell Lines, T2, K562 and K562-A2 cells

T2, K562 and K562-A2 were cultured in RPMI 1640 medium supplemented with 12% FBS, 1× MEM, 2 mM L-glutamine and 1 mM sodium-pyruvate. Volume of the medium was 10 mL in a middle-sized culture flask. Approximately every 4 days, ¾ of the cell suspension was removed and the same volume of fresh medium was added. For the K562-A2 cells, the medium was supplemented with 1 mg/mL of the selection antibiotic G418.

DC Generation and Culture

PBMCs from a donor were isolated by Ficoll density gradient centrifugation. PBMCs were resuspended in RPMI 1640 medium supplemented with 1% autologous plasma at 7.5×10$^6$ cells per T75 culture flask. The flasks were incubated at 37° C. and 5% $CO_2$ for 1 hr. Non-adherent cells were carefully washed away. Adhering monocytes were cultured in 10 mL per flask of dendritic cell medium supplemented with 1% autologous plasma, 800 U/mL GM-CSF and 800 U/mL IL-4. After 3 days of culture, 800 U/mL GM-CSF and 800 U/mL IL-4 were added again. On day 6 of culture, 800 U/mL GM-CSF, 500 U/mL IL-4, 5 ng/mL IL-1β, 9 ng/mL IL-6, 9 ng/mL TNF-a and 2 μM $PGE_2$ per 1 mL were added to the immature DCs to induce maturation. Mature DCs were harvested on day 8 of culture.

Flow Cytometry

Flow cytometry was used to measure the cellular expression of chosen molecules. These molecules are specifically stained with monoclonal antibodies attached to fluorescent dyes. Flow cytometric analysis was performed in the fluorescence-activated cell sorter (FACS™). In the FACSCalibur™, the suspension of stained cells was forced through a nozzle, creating a fine stream of liquid containing cells spaced singly at intervals. As each cell passed through a laser beam, it scattered the laser light and fluorescent molecules associated with the cell were excited. Sensitive photomultiplier tubes detected both the scattered light, which gave information about the size and granularity of the cell, and the fluorescence emissions, which gave information about the binding of the labelled monoclonal antibodies and, hence, the expression of targeted molecules by each cell. For sorting of the cells of interest, a MoFlo™ High-Performance Cell Sorter (Dako, Fort Collins, Colo., USA) was used with 25,000 events/s and max. 1 psi.

Direct Staining of Cell-Surface Molecules

In order to measure the expression of HLA-A2 molecules on the surface, the hybridoma supernatant HB82 (ATCC, Bethesda Md.) and a secondary goat anti-mouse antibody conjugated with PE (phycoerythrin) were used for the direct staining on the cell surface. Approximately $1 \times 10^5$ DCs, K562 or K562-A2 cells were washed once. Each washing step included resuspension of cells in 600 µL of FACS™ buffer, centrifugation at 300×g for 4 min and discarding of the supernatant. After washing, 50 µL of HB82 was added separately to the pellets. After a 30 min incubation period on ice, cells were washed once. Then 0.5 µL of the secondary antibody (1/100 dilution; 0.5 µL antibody in 50 µL FACS™ buffer) were added separately to the pellets. After a 30 min incubation period on ice and in the dark, cells were washed once. Finally, cells were resuspended in 200 µL of FACS™ buffer and flow cytometric analysis was performed.

Indirect Staining of Intracellular Molecules

In order to measure the expression of tyrosinase inside RNA-transfected DCs, cells were first fixed using 1% paraformaldehyde in FACS™ buffer. After the fixation the cells were permeabilised using 0.1% and 0.25% Saponin in FACS™ buffer. Briefly, approximately $3 \times 10^5$ cells were washed once. Each washing step included resuspension of cells in 500 µL of FACS™ buffer or 0.1% Saponin in FACS™ buffer, centrifugation at 300×g for 4 min and discarding of supernatant. After washing, 500 µL of 1% paraformaldehyde in FACS™ buffer (fixation medium) were added to the pellet and mixed gently. After a 30 min incubation period on ice, cells were washed twice with FACS™ buffer. It was possible to store the cells in 500 µL FACS™ buffer at 4° C. up to 7 days. The pellets were washed with 500 µL 0.1% Saponin in FACS™ buffer once. Subsequently, 50 µL of 0.25% Saponin in FACS™ buffer (permeabilisation medium) and 5 µL of the tyrosinase-specific primary antibody were added to the pellet and mixed gently. After a 1 h incubation at room temperature, cells were washed once with 0.1% Saponin in FACS™ buffer and then 0.5 µL of the Cy5-conjugated secondary antibody specific for the primary antibody (1/100 dilution) in 50 µl 0.25% Saponin in FACS™ buffer were added to the pellet and mixed gently. After a 30 min incubation at room temperature in the dark, the cells were washed with 500 µL 0.1% Saponin in FACS™ buffer. Finally, pelleted cells were resuspended in 200 µL of 0.1% Saponin in FACS™ buffer and flow cytometric analysis was performed.

Tetramer Staining and Tetramer Off-Rate

In order to assess the avidity of HLA-A2-restricted tyrosinase-specific CD8$^+$ T cells and to perform a sorting with the MoFlo™ High-Performance Cell Sorter (Dako, Fort Collins, Colo., USA) these T cells were stained with a PE-labeled A*0201/htyr369-377/Hβ$_2$m tetramer (provided by Prof. D. Busch). The cells were washed twice. Each washing step included resuspension of cells in cold PBS+0.5% human serum, centrifugation at 300×g for 5 min and discarding of the supernatant. The incubation volume depends on the cell number. Up to $10^6$ of cells were incubated in 50 µL 25 min with PE-labeled tetramer on ice in the dark (1/25 dilution, 2 µL tetramer in 50 µL PBS+0.5% human serum). For the sorting of HLA-A2-restricted tyrosinase-specific CD8$^+$ T cells up to $5 \times 10^6$ cells were incubated with 6 µL A2/peptide tetramer in 100 µL PBS+0.5% human serum. Then for an additional 25 min in a ratio of 1/50 CD8-APC antibody (BD Pharmingen, Franklin Lakes, USA) was added. After the staining the cells were washed twice and finally either fixed with 1% paraform aldehyde in FACS™ buffer and analysed by flow cytometry FACSCalibur (Becton Dickinson, Mountain View, Calif.) or diluted in PBS+0.5% human serum for sorting of the tetramer$^+$CD8$^+$ T cells in the MoFlo™ High-Performance Cell Sorter (Dako, Fort Collins, Colo., USA).

For tetramer off-rate assays, after washing the rebinding of detached tetramer was prevented by the incubation with saturating amounts of hybridoma supernatant HB82 (ATCC, Bethesda Md.), which binds HLA-A2 independently of the complexed peptide. After increasing time intervals samples were taken, fixed and analysed by flow cytometry for the intensity of tetramer staining.

Production of Single-Species cRNA

Production of single-species in vitro transcribed RNA, designated here as cRNA, included four steps: linearisation of the plasmid containing a cDNA insert, in vitro transcription based on the promoter sequence and the cDNA template in the linearised plasmid, polyadenylation of synthesised cRNA and cRNA purification. Since substantial amounts of the cDNA template, i.e. plasmid DNA (pDNA), were needed for in vitro transcription reactions, the plasmid had to be amplified in competent bacteria.

Transformation of Competent Bacteria with Plasmid DNA

In order to obtain larger amounts of pDNA that was received from other groups as a kind gift, competent bacteria had to be transformed with the pDNA in question and expanded. A 50 µL vial of One Shot TOP10F' competent cells was slowly defrosted on melting ice, a small volume of pDNA was added and mixed with the bacteria by tapping gently. The cells were incubated on ice for 30 min, then heated at 42° C. for exactly 30 sec and finally placed on ice to cool for 2 min. Rich SOC medium, provided together with the competent cells, was added and transformed bacteria were plated onto LB medium agar plates with the appropriate selection antibiotic. Plates were placed into the bacterial incubator overnight at 37° C. Since the antibiotic zeocin is light sensitive and its activity is inhibited by high salt concentrations, plates for bacteria transformed with pZeoSV2+/huTyr contained low-salt LB agar medium and were stored in the dark.

Selection and Expansion of Transformed Bacteria

Only bacteria transformed with pDNA, encoding resistance to an antibiotic, were able to grow and form colonies on selection plates despite the presence of the corresponding antibiotic in the agar medium. After overnight growth, colonies were plucked from the plates using sterile tooth-picks. Each individual colony was inoculated into 5 mL of LB medium containing the appropriate antibiotic in a 15 mL Falcon tube. If previously selected and frozen transformed bacteria were to be expanded, frozen vials were transferred from the –80° C. freezer onto melting ice. Approximately 5 µL of the partially thawed bacterial suspension were then transferred into a 15 mL Falcon tube containing 5 mL of LB medium with the appropriate antibiotic. The tubes were incubated overnight (approximately 12 hr) at 37° C. with vigorous shaking at 150 rpm for efficient growth of transformed bacteria.

Freezing of Transformed Bacteria

Bacteria are the least harmed by the freezing process if the freezing medium contains 15% of glycerin. Therefore, 400 µL of the overnight bacterial suspension were added to 84 µL of autoclaved 87% glycerin, vortexed, quickly frozen in liquid nitrogen and transferred to –80° C.

Plasmid DNA Extraction from Transformed Bacteria

After overnight culture, bacterial suspensions were centrifuged at 5300×g and 4° C. for 10 min. Plasmid DNA extraction from bacterial cells was performed using the QIAwell® 8 Ultra Plasmid Kit, according to manufacturer's instructions. Briefly, pelleted cells were lysed. The salt and pH conditions in the lysates ensured exclusive binding of DNA to the membrane, while degraded RNA and cellular proteins were not retained. The membrane was then washed with a buffer which disrupts any DNA-protein interactions allowing the removal of any nucleic acid-binding proteins and other residual contaminants from the pDNA. Additional washing steps removed salts and other non-DNA constituents. Purified pDNA was finally eluted in Tris buffer. The yield of extracted pDNA was 4-8 μg per 5 mL of overnight bacterial culture, depending on the plasmid.

In Vitro Transcription of Single-Species cDNA into cRNA

Each plasmid was linearised with the appropriate restriction enzyme in order to produce a template suitable for in vitro transcription. Since all plasmids contained the T7 promoter at the 5' end of cDNA encoding the desired protein, transcription was performed using the T7 RNA polymerase from the mMESSAGE mMACHINE™ T7 kit according to manufacturer's instructions. Stability of an RNA molecule and its efficient use as a template for translation into protein depend on the presence of a cap at its 5' end and a poly(A) tail at the 3' end. A poly(A) tail is always part of a mRNA molecule synthesised by a cell. Therefore, the total cellular mRNA amplification procedure, described above, included only the addition of a cap analogue in the in vitro transcription reaction. However, single-species cRNA produced using cDNA in a plasmid may or may not contain a poly(A) tail, depending on whether the tail is encoded in the construct or not. In addition to integrating a cap analogue at the 5' end in the in vitro transcription reaction, tyrosinase, HLA-A2 cRNAs were polyadenylated at the 3' end using the Poly(A) Tailing Kit. Both reactions were performed under conditions suggested by the manufacturer. After in vitro transcription and cRNA purification, the measured yield of cRNA was 60-70 μg per 100 μL of the polyadenylation reaction mixture.

Purification of cRNA

Purification of cRNA, obtained in in vitro transcription reactions using as a template either amplified total cellular cDNA or single-species cDNA in a plasmid, was performed using the RNeasy® Mini Kit according to manufacturer's instructions. For purification, the procedure started with the transfer of the in vitro transcription reaction mixture onto an RNeasy® column. RNA was eluted in DEPC water and aliquots were stored at −80° C.

RNA Transfection into DCs

The cellular plasma membrane serves the vital function of separating the molecular contents of the cell from its external environment. The membranes are largely composed of amphiphilic lipids which self-assemble into a highly insulating bilayer. On their quest to capture as much antigen as possible, immature DCs are well known to take up various structures (ranging in size from small molecules to apoptotic bodies) from their surroundings, including RNA. They do so through macropinocytosis and endocytosis. Even though simple DC co-incubation with RNA has been shown to achieve T-cell priming, more aggressive methods such as lipofection and electroporation proved to be better transfection methods.

Electroporation

Electroporation induces reversible permeability of plasma membranes when cells are exposed to short pulses of strong external electric fields. The formation of hydrophilic pores is a result of reorientation of lipids in the bilayer membrane. The molecular mechanism of this phenomenon is still not well understood. The number of pores and their diameter increases with the product of the pulse amplitude and the pulse duration. Whereas small molecules simply diffuse through the pores into the cytoplasm, larger molecules, like nucleic acids, are driven into the cell by electrophoretic forces. It has also been shown that the presence of nucleic acids facilitates pore formation. Pores appear within a microsecond of exposure to the electric field, but it takes minutes for them to reseal.

First, $2\text{-}3\times10^6$ DCs or K562 cells were resuspended in at least 170 μL OptiMEM I medium, were put into a 0.4 cm electroporation cuvette and incubated on ice for approximately 3 min. Cooling the suspension before electroporation was advantageous because it slowed down the cellular metabolism. Thereby, overheating due to electricity was prevented. Furthermore, damage caused by the electric shock and by molecules released from dead cells was minimised. Subsequently, RNA, resuspended in no more than 100 μL of DEPC water was added, giving a total electroporation suspension volume of 270 μL. The suspension was shortly mixed by pipetting and then quickly electroporated. Electroporation was performed with 250 V and 150 μF. Immediately after electroporation, cells were transferred into the dendritic cell medium supplemented with 2% autologous plasma, 10 mM HEPES, 800 U/mL GM-CSF and 800 U/mL IL-4. The cells were counted and the suspension was quickly aliquoted for either FACS™ analyses, RNA isolation or functional assays and placed into the incubator at 37° C. and 5% $CO_2$.

Functional Assay

In the functional assay, RNA-transfected DCs or K562 cells, peptide-pulsed DCs or tumour cells served as stimulators. Antigen-specific CTL clones served as effectors. In order to measure the stimulatory capacities of stimulators, DCs or other cells were first co-incubated with the T cells, which were harvested and used in co-incubation cultures 8-14 days after thawing and restimulation. The amount of IFN-γ secreted by activated T cells was measured in the enzyme-linked immunosorbent assay (ELISA).

Peptide-Pulsed T2 Cells Co-Incubation with T cells

For co-incubation of T2 cells with CTLs, lower cell numbers were taken. For the exogenous peptide pulsing, $1\times10^6$ T2 cells were incubated with 10 μg/mL YMD tyrosinase peptide (YMDGTMSQV (SEQ ID NO: 1, Gene Center, LMU, Munich) and 10 μg/mL human $\beta_2$-Microglobulin (Calbiochem, San Diego, United States). Every 20 minutes the cell suspensions were shaken. After a 2 h incubation at 37° C. and 5% $CO_2$, the cell suspension was washed once to remove unbound peptide. 100 μL of the peptide-pulsed T2 suspension ($1\times10^4$ cells in RPMI 1640 supplemented with 12% FCS) was co-incubated with 100 μL of the CTL suspension ($2\times10^3$ cells in CTL medium supplemented with 15% human serum), giving a 5:1 stimulator to effector ratio.

After a 24 h co-incubation of effectors and stimulators, 150 μL of each supernatant was harvested and stored at −20° C. The supernatant was analysed in the enzyme-linked immunosorbent assay (ELISA).

DC or K562 Co-Incubation with T Cells

Either 12 hr or 24 hr after electroporation, 100 μL of the T cell suspension ($2\times10^4$ cells in co-incubation medium) were added to 100 μL of the transfected-cell suspension ($2\times10^4$ or $4\times10^4$ cells in dendritic cell medium supplemented with 2% autologous plasma and 800 U/mL GM-CSF and 800 U/mL IL-4), giving a total of 200 μL per well of a 96-well plate and 1:4, 1:2, 1:1, 2:1 or 4:1 stimulator to effector ratios.

Untransfected DCs were exogenously pulsed with peptides by adding 10 μL of the peptide solution (100 μL/mL) to 100 μL of the DC suspension ($4\times10^4$ cells in dendritic cell medium supplemented with 2% autologous plasma and 800 U/mL GM-CSF and 800 U/mL IL-4). After a 2 hr incubation at 37° C. and 5% $CO_2$, 100 pt. of the CTL suspension ($2\times10^4$ cells in CTL co-incubation medium) were added, giving a 2:1 stimulator to effector ratio. After a 24 hr co-incubation of effectors and stimulators, 150 μL of each supernatant was harvested and stored at −20° C.

Interferon-Gamma (IFN-γ) ELISA

The measurement of IFN-γ in the co-culture supernatants was performed in ELISA using the OptEIA™ Human IFN-γ Set according to manufacturer's instructions. Briefly, the ELISA plates were coated with a mouse anti-IFN-γ capture antibody and then blocked with an FBS-containing solution. In some cases, supernatants were diluted 1:2.5 in the co-incubation medium. The same medium was used to make serial dilutions of the IFN-γ standard. After IFN-γ from cell culture supernatants or standard solutions bound to the capture antibodies in the plates, the biotinylated mouse anti-IFN-γ detection antibody was added together with avidin conjugated to horseradish-peroxidase. To visualise the complexes consisting of capture antibody, IFN-γ, detection antibody, biotin, avidin and horseradish-peroxidase, $H_2O_2$ (a substrate for peroxidase) in combination with tetramethylbenzidine (substrate reagents A and B mixed) was added, changing the solution colour into blue. The enzymatic reaction was stopped with 1 M ortho-phosphoric acid. Thereby, the colour of the solution turned yellow, its intensity being directly proportional to the amount of substrate processed, i.e. indirectly proportional to the amount of IFN-γ captured. Light absorption in the reaction solution was measured at 450 nm. Unknown IFN-γ concentrations were calculated with the help of a standard curve which was drawn based on known concentration of the IFN-γ standard and corresponding measured absorbances.

Cytotoxicity Assay

Cytolytic activity of the tetramer$^+$CD8$^+$ sorted bulk cell line and T cell clones respectively was analysed in a standard 4 h chromium release assay. The two HLA-matched melanoma cell lines Mel A375 (HLA-A2-positive, tyrosinase-negative) and Mel IL-2 (HLA-A2-positive, tyrosinase-positive) were used. Briefly, $10^6$ target melanoma cells were labeled with 200 μCi $^{51}$Cr for 1-1.5 h. $^{51}$Cr-labeled target cells were cultured with T cells in 100 μL/well RPMI 1640 with 12% FCS in V-bottom 96-well tissue culture plates (Greiner, Solingen, Germany). To evaluate the efficacy of CTL-mediated lysis, T cells were serially diluted and then cocultured with $10^3$ target cells/well to provide graded effector cell to target cell (E:T) ratios. After 4 h coculture at 37° C., 50 μL of supernatant were collected and radioactivity was measured in a gamma counter. The percentage of specific lysis was calculated as: 100×(experimental release−spontaneous release)/(maximum release−spontaneous release). Spontaneous release was assessed by incubating target cells in the absence of effector cells and generally less than 14%.

REFERENCES

Becker, C., Pohla, H., Frankenberger, B., Assenmacher, M., Schendel, D. J. and Th. Blankenstein. 2001. Adoptive tumor therapy with T lymphocytes enriched through an IFN capture assay. *Nature Med.* 7(10): 1159-1162.

Dudley, M. E., Wunderlich, J. R., Robbins, P. F., Yang, J. C., Hwu, P., Schwartzentruber, D. J., Topalian, S. L., Sherry, R., Restifo, N. P., Hubicki, A. M., Robinson, M. R., Raffeld, M., Duray, P., Seipp, C. A., Rogers-Freezer, L., Morton, K. E., Mavroukakis, S. A., White, D. E., Rosenberg, S. A. (2002). Cancer regression and autoimmunity in patients after clonal repopulation with antitumor lymphocytes. *Science* 298:850-854.

Dudley, M. E. and Rosenberg, S. A. (2003). Adoptive-cell-transfer therapy for the treatment of patients with cancer. *Nature Reviews Cancer* 3: 666-675.

Engels, B., Nössner, E., Frankenberger, B., Blankenstein, Th., Schendel, D. J., and W. Uckert. 2005. Redirecting human T lymphocytes towards renal cell carcinoma-specificity by retroviral transfer of T cell receptor genes. *Human Gene Ther.*, 16(7):79.9-810

Falk, C. S, and Schendel, D. J. (2002). Allogeneic MHC class I ligands and their role in positive and negative regulation of human cytotoxic effector cells. *Human Immunol.* 63:8-19.

Gao, L., Bellantuono, I., Elsasser, A., Marley, S. B., Gordon, M. Y., Goldmann, J. M., Stauss, H. J. (2000). Selective elimination of leukemic CD34+ progenitor cells by cytotoxic T lymphocytes specific for WT1. *Blood* 95: 2198-2203.

Gao, L., Yang, T. H., Tourdot, S., Sadovnikova, E., Hasserjian, R. and Stauss H. J. (1999). Allo-major-histocompatibility complex restricted cytotoxic T lymphocytes engraft in bone marrow transplant recipients without causing graft-versus-host disease. *Blood* 94: 2999-3006.

Geiger, C., Regn, S., Noessner, E., Wilde, S., Frankenberger, B., Papier, B., Pohla, H., and D. J. Schendel. 2005. Development of a generic RNA-pulsed dendritic cell vaccine for renal cell carcinoma, *J. Translational Medicine in press.*

Gilboa-E and J. Viewig. 2004. Cancer immunotherapy with mRNA-transfected dendritic cells. *Immunol. Rev.* 199:251-63.

Kolb, H. J., Schmid, C., Barrett, A. J. and Schendel, D. J. (2004). Graft-versus-leukemia reactions in allogeneic chimeras. *Blood* 103:767-776.

Kolb, H. J., Schattenberg, A., Goldman, J. M., Hertenstein, B., Jacobsen, H., Arcese W., Ljungman, P., Ferrant, A., Verdonck, L. Niederwieser, B. et al. 1995. Graft-versus-leukemia effect of donor lymphocyte transfusions in marrow grafted patients. *Blood* 86:2041.

Levings, M. K. and M. G. Roncarolo. 2005. Phenotypic and functional differences between human CD4+CD25+ and type 1 regulatory T cells. *Curr. Top. Microbiol. Immunol.* 293:303-326.

Liao, X., Yongging, L., Bonini, C., Nair, S., Gilboa, E., Greenberg, P. D., Yee, C. (2004). Transfection of RNA encoding tumor antigens following maturation of dendritic cells leads to prolonged presentation of antigen and the generation of high-affinity tumor-reactive cytotoxic T lymphocytes. *Mol. Ther.* 9: 757-764.

Nair, S. K., Boczkowski, D., Morse, M., Cumming, R. I., Lyerly, H. K. and Gilboa, E. (1998). Induction of primary carcinoembryonic antigen (CEA)-specific cytotoxic T lymphocytes in vitro using human dendritic cells transfected with RNA. *Nat. Biotechnol.* 16(4): 364-369.

Napolitani, G., Rinaldi, A., Bertoni, F., Salllusto, F. and A. Lanzavecchia. 2005. Selected Toll-like receptor agonist combinations synergistically trigger a T helper type-1 polarizing programme in dendritic cells. *Nat. Immunol.* 6(8): 769-76.

Regn, S., Chen, X., Schendel, D., Kolb, H.-J. and M. A. Roskrow. 2001. The generation of monospecific and bispecific anti-viral cytotoxic T lymphocytes (CTL) for the prophylaxis of patients receiving an allogeneic bone marrow transplant. *Bone Marrow Transplant.* 27: 53-64.

Schaft, N, Dorrie, J., Thuman, P., Beck, V. E., Muller, I., Schultz, E. S., Kampgen, E., Dieckmann, D. and Schuler, G. 2005. Generation of an optimized polyvalent monocyte-derived dendritic cell vaccine by transfecting defined RNA after rather than before maturation. *J. Immunol.* 174(5): 3087-97.

Schendel, D. J., Wank, R. and B. Dupont. 1979. Standardization of the human in vitro cell-mediated lympholysis technique. *Tissue Antigens* 13: 112-120.

Schendel, D. J., Maget, B., Falk, C. S. and R. Wank. Human CD8$^+$ T lymphocytes. 1997. In: The Immunology Methods Manual. (I. Lefkovits, Ed.) pp 670-690, Academic Press Ltd., London.

Su, Z., Peluso, M. V., Raffegerst, S. H., Schendel, D. J., and M. A. Roskrow. 2001. LMP2a-specific cytotoxic T lymphocytes for the treatment of patients with relapsed EBV-positive Hodgkin disease. *Eur. J. Immunol.* 31: 947-958.

Su, Z., Peluso, M. V., Raffergerst, S. H., Schendel, D. J. and Roskrow, M. 2002. Antigen presenting cells transfected with LMP2a RNA induce CD4+ LMP2a-specific cytotoxic T lymphocytes which kill via a Fas-independent mechanism. *Leuk. Lymphoma* 43(8): 1651-62.

Toes, R. E., Schoenberger, S. P., van der Voort, E. I., Offringa, R. and Melief, C. J. 1998. CD40-CD40Ligand interactions and their role in cytotoxic T lymphocyte priming and anti-tumor immunity. *Semin. Immunol.* 10(6): 443-8.

Yee, C., Savage, P. A., Lee, P. P., Davis, M. M. and P. D. Greenberg. 1999. Isolation of high avidity melanoma-reactive CTL from heterogenous populations using peptide-MHC-tetramers. J. Immunol. 162(4): 2227-34.

FURTHER REFERENCES

Belinda Palermo, Silvia Garbelli, Stefania Mantovani, Elisabetta Scoccia, Gian Antonio Da Prada, Paola Bernabei, M. Antonietta Avanzini, Valeria Brazzelli, Giovanni Borroni and Claudia Giachino (2005). Qualitative difference between the cytotoxic T lymphocyte responses to melanocyte antigens in melanoma and vitiligo. Eur. J. Immunol. 35: 3153-3162.

Cassian Yee, Peter A. Savage, Peter P. Lee, Mark M. Davis, and Philip D. Greenberg (1999). Isolation of High Avidity Melanoma-Reactive CTL from Heterogeneous Populations Using Peptide-MHC Tetramers. The Journal of Immunology: 2227-2234.

Matthias Wölfl, Stefan Schalk, Martin Hellmich, Katharina M. Huster, Dirk H. Busch, and Frank Berthold (2004). Quantitation of MHC Tetramer-Positive Cells From Whole Blood: Evaluation of a Single-Platform, Six-Parameter Flow Cytometric Method. Wiley-Liss, Inc. Cytometry Part A 57A:120-130.

d) selecting antigen-specific T cells which are specific for an MHC-antigen ligand that comprises the patient-derived MHC molecule bound to the antigen.

2. The method of claim 1, wherein the APCs are selected from the group consisting of dendritic cells, activated B cells, monocytes, macrophages, and activated T cells.

3. The method of claim 1, wherein the MHC molecule and the antigen are present as a mixture of antigen and nucleic acid encoding the MHC molecule.

4. The method of claim 1, wherein the antigen is selected from the group consisting of pathogenic agents derived from viruses, bacteria, protozoa, parasites, tumor cells, tumor cell associated antigens, autoantigens and functional parts thereof.

5. The method of claim 4, wherein the viruses are selected from the group consisting of influenza viruses, measles and respiratory syncytial viruses, dengue viruses, human immunodeficiency viruses, human hepatitis viruses, herpes viruses, papilloma viruses, and wherein the protozoa is *Plasmodium falciparum*, and the bacteria is tuberculosis-causing Mycobacteria.

6. The method of claim 4, wherein the tumor associated antigen is selected from hematological malignancies and solid tumors.

7. The method of claim 6, wherein said solid tumors are selected from the group consisting of colon carcinoma, breast carcinoma, prostate carcinoma, renal cell carcinoma (RCC), lung carcinoma, sarcoma and melanoma.

8. The method of claim 1, wherein the selecting in step d) comprises measuring the cytokine secretion of the T cells or other measures of T cell activation.

9. The method of claim 1, further comprising expanding the antigen-specific T cells selected in step d) ex vivo.

10. The method of claim 1, further comprising cloning the T cell receptor (TCR) of the antigen-specific T cells selected in step d).

The invention claimed is:

1. A method of generating antigen specific T cells, comprising:
   a) providing a nucleic acid encoding a patient-derived MHC molecule; and an antigen or a second nucleic acid encoding said antigen;
   b) co-transfecting or introducing both compounds as defined in a) into antigen presenting cells (APCs) derived from a healthy donor who is allogeneic to the patient;
   c) priming peripheral blood lymphocytes (PBLs) derived from the healthy donor with said APCs; and 11. The method of claim 10, further comprising expressing the TCR as a transgene in a PBMC.

12. The method of claim 1, wherein the nucleic acid encoding the patient-derived MHC molecule and the antigen is provided as a bicistronic RNA encoding both the patient-derived MHC molecule and the antigen.

13. The method claim 1, wherein the MHC molecule is an MHC class I molecule or is an MHC class II molecule.

14. The method of claim 13, wherein the MHC class I molecule is selected from the group consisting of HLA-A, HLA-B, HLA-C and HLA-E.

15. The method of claim 13, wherein the MHC class II molecule is selected from the group of HLA-DP, HLA-DQ and HLA-DR.

16. The method of claim 1, wherein the APCs derived from the healthy donor are dendritic cells.

17. A method of generating antigen T cells specific for a particular HLA-A, HLA-B, HLA-C or HLA-E class I MHC molecule bound to a solid tumor cell associated antigen, comprising:
- a) providing a nucleic acid encoding an HLA-A, HLA-B, HLA-C or HLA-E class I MHC molecule from a patient having a solid tumor, and further providing a solid tumor cell associated antigen or nucleic acid encoding a solid tumor cell associated antigen;
- b) co-transfecting or introducing both components as defined in (a) into dendritic cells derived from a healthy donor who is allogeneic for the HLA-A, HLA-B, HLA-C or HLA-E class I MHC molecule;
- c) priming peripheral blood lymphocytes (PBLs) derived from the healthy donor with the dendritic cells; and
- d) using a tetramer comprising the particular HLA-A, HLA-B, HLA-C or HLA-E class I MHC molecule bound to a peptide of the solid tumor cell associated antigen to select for those T cells which are specific for the particular HLA-A, HLA-B, HLA-C or HLA-E class I MHC molecule bound to the solid tumor cell associated antigen.

* * * * *